(12) United States Patent
Schrader et al.

(10) Patent No.: US 11,191,273 B2
(45) Date of Patent: Dec. 7, 2021

(54) METHODS OF MAKING PYRANOPYRANS SUCH AS PYRANOPYRAN NITRILE AND METHODS OF USING PYRANOPYRANS SUCH AS PYRANOPYRAN NITRILE

(71) Applicants: The United States of America, as Represented by the Secretary of Agriculture, Washington, DC (US); Villanova University, Villanova, PA (US)

(72) Inventors: Kevin Schrader, Oxford, MS (US); Stephen O. Duke, Oxford, MS (US); Robert M. Giuliano, Wayne, PA (US)

(73) Assignees: The United States of America, as represented by The Secretary of Agriculture, Washington, DC (US); Villanova University, Villanova, PA (US)

( * ) Notice: Subject to any disclaimer, the term of this patent is extended or adjusted under 35 U.S.C. 154(b) by 0 days.

(21) Appl. No.: 16/579,065

(22) Filed: Sep. 23, 2019

(65) Prior Publication Data
US 2020/0093132 A1 Mar. 26, 2020

Related U.S. Application Data

(60) Provisional application No. 62/735,444, filed on Sep. 24, 2018.

(51) Int. Cl.
*C07D 493/04* (2006.01)
*A01N 43/90* (2006.01)
(52) U.S. Cl.
CPC .......... *A01N 43/90* (2013.01); *C07D 493/04* (2013.01)

(58) Field of Classification Search
CPC .............................. A01N 43/90; C07D 493/04
USPC ......................................................... 549/414
See application file for complete search history.

(56) References Cited

PUBLICATIONS

Evidente et al , Diplopyrone, a new phytotoxic tetrahydropyranpyran-2-one produced by Diplodia mutila, a fungus pathogen of cork oak, (Journal of Natural Products , 66(2), p. 313-315 (Year: 2003).*
Gomez et al ,A novel entry to naturally occurring 5-alkenyl α,β-unsaturated δ-lactones from D-glucose: syntheses of (+)-and (+)-asperlin Chemical Communications (Cambridge) , (17), 1647-1648. (Year: 1997).*

(Continued)

*Primary Examiner* — Taylor V Oh
(74) *Attorney, Agent, or Firm* — Ariel L. Atkinson; John D. Fado

(57) ABSTRACT

Disclosed herein are methods of making (4aR,6S,8aR)-6-((R)-1-hydroxyethyl)-6,8a-dihydropyrano[3,2-b]pyran-2-(4aH)-one (2) and methods of making (4aR,6S,8aR)-6-cyano-6,8a-dihydropyrano-[3,2-b]pyran-2(4aH)-one (4). Other pyranopyrans were also synthesized. Also compositions containing (4aR,6S,8aR)-6-cyano-6,8a-dihydropyrano-[3,2-b]pyran-2(4aH)-one (4) (or other pyranopyrans described herein) and optionally a carrier. In addition, methods for killing microorganisms or weeds on or in an object or area involving contacting the object or area with an effective microorganisms or weeds killing amount of a composition containing (4aR,6S,8aR)-6-cyano-6,8a-dihydropyrano-[3,2-b]pyran-2(4aH)-one (4) (or other pyranopyrans described herein) and optionally a carrier.

6 Claims, 7 Drawing Sheets
(4 of 7 Drawing Sheet(s) Filed in Color)

(+)-Diplopyrone (1)

Pyranopyran (2)

Pyranopyran Acetate (3)

Pyranopyran Nitrile (4)

(56) References Cited

PUBLICATIONS

Egidio Giorgio et al., "Absolute Configuration of (+)-Diplopyrone", Journal, 2005, 7-13, 70 (1), J. Org. Chem, Italy.
Marco Fuse et al., "Unbiased Determination of Absolute Configuralions by vis-à-vis Comparison of Experimental and Simulated Spectra: The Challenging Case of Diplopyrone", Journal, 2019, 9230-9237, 123, J. Phys, Chem. B, Italy.

* cited by examiner (+)-Diplopyrone (1)

Pyranopyran (2)

Pyranopyran Acetate (3)

Pyranopyran Nitrile (4)

I　　　　　II (Chelation control)　　　　　III (Felkin-Anh)

METHODS OF MAKING PYRANOPYRANS SUCH AS PYRANOPYRAN NITRILE AND METHODS OF USING PYRANOPYRANS SUCH AS PYRANOPYRAN NITRILE

REFERENCE TO RELATED APPLICATION

This application claims the benefit of U.S. Provisional Application No. 62/735,444, filed 24 Sep. 2018, which is incorporated herein by reference in its entirety.

BACKGROUND OF THE INVENTION

Disclosed herein are methods of making (4aR,6S,8aR)-6-((R)-1-hydroxyethyl)-6,8a-dihydropyrano[3,2-b]pyran-2-(4aH)-one (2) and methods of making (4aR,6S,8aR)-6-cyano-6,8a-dihydropyrano-[3,2-b]pyran-2(4aH)-one (4). Other pyranopyrans were also synthesized. Also compositions containing (4aR,6S,8aR)-6-cyano-6,8a-dihydropyrano-[3,2-b]pyran-2(4aH)-one (4) (or other pyranopyrans described herein) and optionally a carrier. In addition, methods for killing microorganisms or weeds on or in an object or area involving contacting the object or area with an effective microorganisms or weeds killing amount of a composition containing (4aR,6S,8aR)-6-cyano-6,8a-dihydropyrano-[3,2-b]pyran-2(4aH)-one (4) (or other pyranopyrans described herein) and optionally a carrier.

Diplopyrone is a phytotoxin isolated from the fungus *Diplodia mutila* and reported by Evidente et al. in 2003 (Evidente, A., et al., J. Nat. Prod., 66: 313-315 (2003); Giorgio, E., et al., J. Org. Chem., 70: 7-13 (2005)). It is an endophytic fungus, meaning it can reside in the host plant for a period of time before causing damage (Tan, R. X., and W. X Zou, Nat. Prod. Rep., 18: 448-459 (2001)). *D. mutila* is thought to be responsible for cork oak decline in parts of southern Europe where the disease has caused large and negative economic and environmental impacts. Diplopyrone causes necrosis and wilting of cork oak (*Quercus suber*) cuttings and is considered the main phytotoxin responsible for the observed pathogenesis. Strains of this fungus also infect other oak species as well as cypress. Recently, there have been studies of structure-activity relationships of fungal phytotoxins, in particular the relationship of stereochemistry to biological activity (Evidente, A., et al., Chirality, 25: 59-78 (2013); Evidente, A., et al., Chirality, 23: 674-693 (2011)). These studies provide insight into the mechanisms of action of microbially-derived natural products and may also lead to the identification of new molecular targets for the development of environmentally benign herbicides (Cimmino, A., et al., Nat. Prod. Rep., 32: 1629-1653 (2015); Meepagala, K. M., J. Agric. Chem. Environ., 5: 12-22 (2016); Duke, S. O., et al, Pestic. Biochem. Physiol., 100: 41-50 (2011).

The proposed structure of diplopyrone contains an unusual cis-fused pyranopyran core and was assigned on the basis of spectroscopic data and theoretical calculations of its optical properties as 6-[(1S)-1-hydroxyethyl]-2,4a(S),6(R),8a(S)-tetrahydropyrano-[3,2-b]-pyran-2-one (1) (FIG. 1) (Giorgio, E., et al., 2005). Pyranopyrans (Giuliano, R. M., Curr. Org. Chem., 18: 1686-1700 (2014)) such as those found in brevitoxin and other polyether natural products as well as in okadaic acid, thyrsiferol and other natural products are typically trans-fused, consistent with biosynthetic origins by nucleophilic ring opening of polyepoxides (Vilotijevic, I., and T. F. Jamison, Mar. Drugs, 8: 763-809 (2010)). The first synthesis of the putative structure of (+)-diplopyrone (1) was achieved in 17 steps from cis-1,4-butenediol in 2017 and produces mixtures of diastereomers (Maity, S., et al., J. Org. Chem., 82: 4561-4568 (2017)). Key steps in the synthesis are the Sharpless asymmetric epoxidation, Pd-catalyzed regioselective epoxide opening, tandem iodine-catalyzed allylation/cyclization for dihydropyran synthesis, and α-aminohydroxylation in the presence of L-proline to introduce the C-9 hydroxyl group stereoselectively (7:3 ratio). A comparison of NMR spectral data for their synthetic diplopyrone with that reported for the natural product revealed discrepancies in proton and carbon chemical shifts and led the authors to suggest that revisions to the proposed structure of diplopyrone are necessary. Natural material is scarce (Evidente et al. 2002, Giorgio et al. 2005), thereby increasing the need for compounds to be made available through synthesis to support structural verification and biological studies.

We describe herein the first synthesis of enantiomeric (−)-diplopyrone, pyranopyran (2) based on the structure originally proposed for the natural product. We also describe the first synthesis of pyranopyran nitrile (4). Other pyranopyrans were also synthesized.

SUMMARY OF THE INVENTION

Disclosed herein are methods of making (4aR,6S,8aR)-6-((R)-1-hydroxyethyl)-6,8a-dihydropyrano[3,2-b]pyran-2-(4aH)-one (2) and methods of making (4aR,6S,8aR)-6-cyano-6,8a-dihydropyrano-[3,2-b]pyran-2(4aH)-one (4). Other pyranopyrans were also synthesized. Also compositions containing (4aR,6S,8aR)-6-cyano-6,8a-dihydropyrano-[3,2-b]pyran-2(4aH)-one (4) (or other pyranopyrans described herein) and optionally a carrier. In addition, methods for killing microorganisms or weeds on or in an object or area involving contacting the object or area with an effective microorganisms or weeds killing amount of a composition containing (4aR,6S,8aR)-6-cyano-6,8a-dihydropyrano-[3,2-b]pyran-2(4aH)-one (4) (or other pyranopyrans described herein) and optionally a carrier.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary

Exemplary

Exemplary

Exemplary

Exemplary

Exemplary

is at 0.3 µM on the graph. The Y axis is the percent growth increase after exposure to the test compounds.

Figure 7:
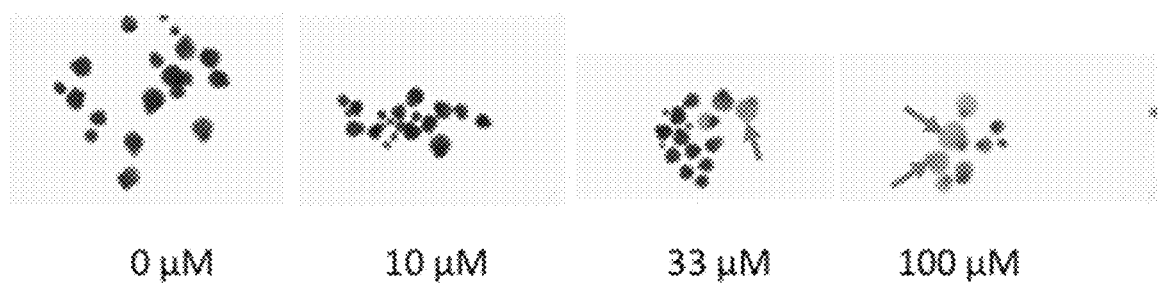

Exemplary FIG. 7 shows the visual symptoms of the effects of pyranopyran nitrile (4) on the growth of *Lemna paucicostata* after 7 days of exposure at different concentrations as described below. Arrows indicate necrotic plants.

DETAILED DESCRIPTION OF THE INVENTION

Disclosed herein are methods of making (4aR,6S,8aR)-6-((R)-1-hydroxyethyl)-6,8a-dihydropyrano[3,2-b]pyran-2-(4aH)-one (2) and methods of making (4aR,6S,8aR)-6-cyano-6,8a-dihydropyrano-[3,2-b]pyran-2(4aH)-one (4). Other pyranopyrans were also synthesized. Also compositions containing (4aR,6S,8aR)-6-cyano-6,8a-dihydropyrano-[3,2-b]pyran-2(4aH)-one (4) (or other pyranopyrans described herein) and optionally a carrier. In addition, methods for killing microorganisms or weeds on or in an object or area involving contacting the object or area with an effective microorganisms or weeds killing amount of a composition containing (4aR,6S,8aR)-6-cyano-6,8a-dihydropyrano-[3,2-b]pyran-2(4aH)-one (4) (or other pyranopyrans described herein) and optionally a carrier.

Herein we describe the first synthesis of enantiomeric (−)-diplopyrone, pyranopyran (2), based on the structure originally proposed for the natural product. The synthesis was carried out in 13 steps from a commercially available derivative of D-galactose. We also describe the syntheses of pyranopyran nitrile (4) in 8 steps from tri-O-acetyl-D-galactal. Remarkably both syntheses were highly stereoselective and both are amenable for the preparation of additional compounds for use in biological studies. X-ray crystallographic analysis has been obtained for nitrile pyranopyran (4). The crystallographic analyses coupled with NMR data provide further insight into the structure assignments for natural and synthetic diplopyrones in the literature. Biological assays were carried out at the USDA Natural Products Utilization Research Unit. Compounds (2), (3), and (4) were tested for phytotoxic, fungicidal, and antibacterial activity, the latter against common bacterial pathogens in fish. Surprisingly nitrile pyranopyran (4) was significantly more active than a commercially used antibiotic used against *Edwardsiella ictaluri*, a common pathogen in catfish. Results of these bioassays are presented herein.

For example, enantiomeric (−)-diplopyrone, pyranopyran (2) can be produced based on the following reactions (13 steps from a commercially available derivative of D-galactose):

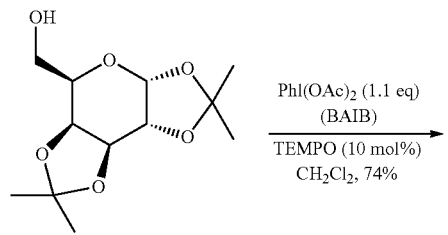

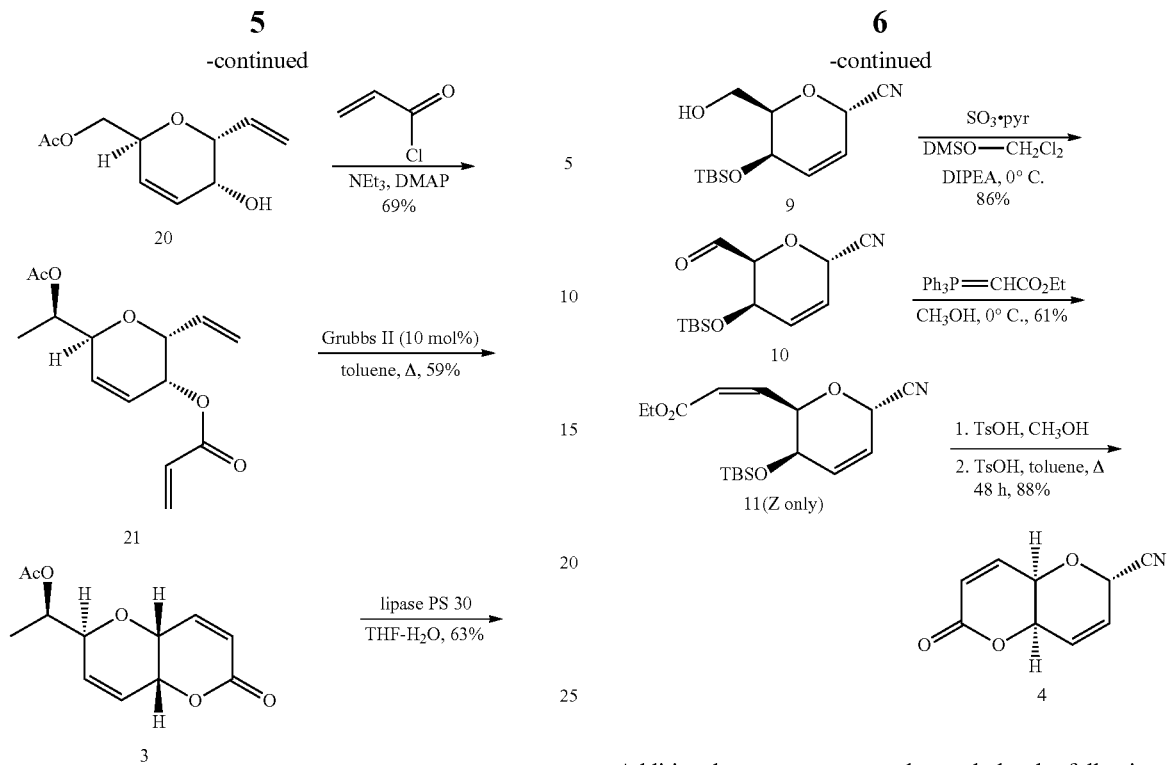
For example, pyranopyran nitrile (4) can be produced based on the following reactions (8 steps from tri-O-acetyl-D-galactal):
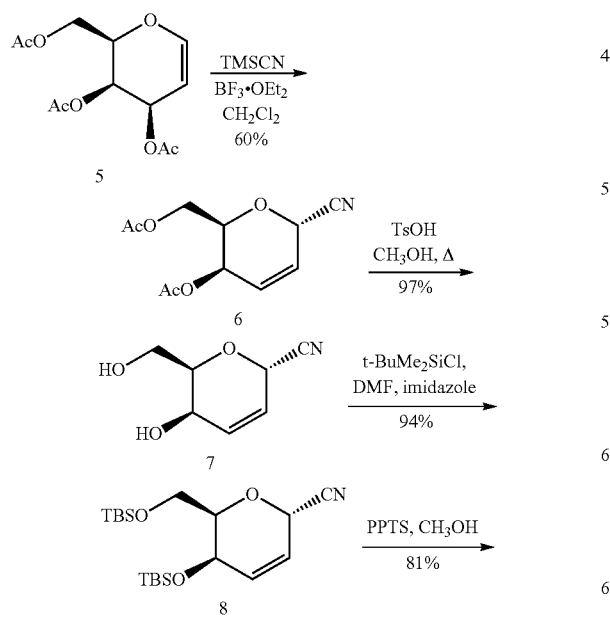
Additional pyranopyrans can be made by the following:
Scheme 5. Synthesis of (-)-Desmethyldiplopyrone 28
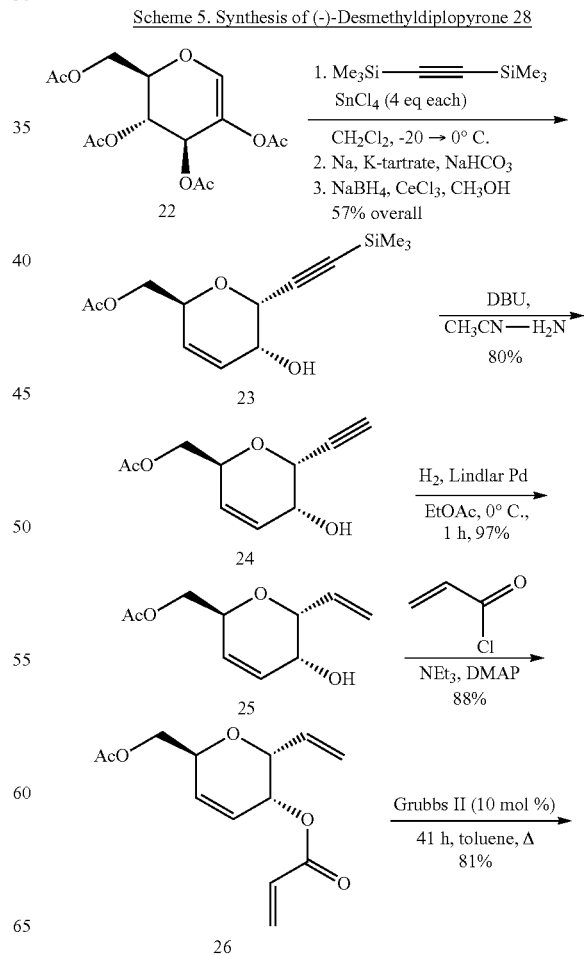

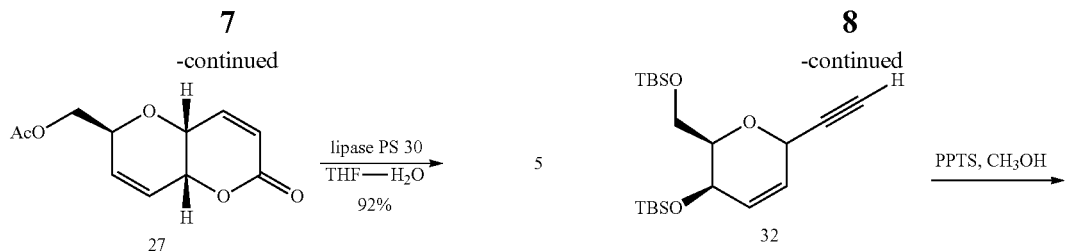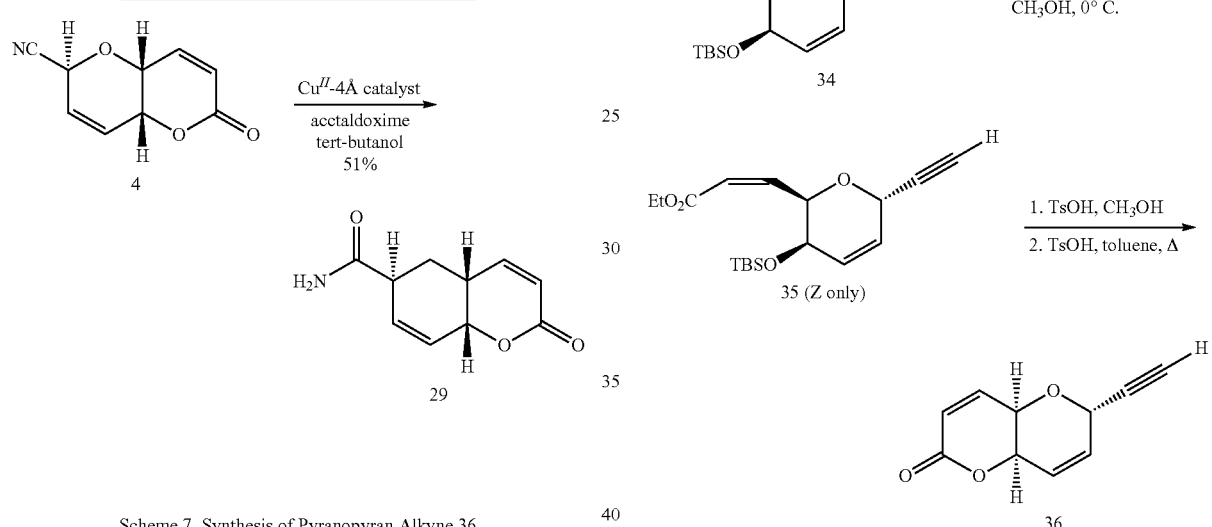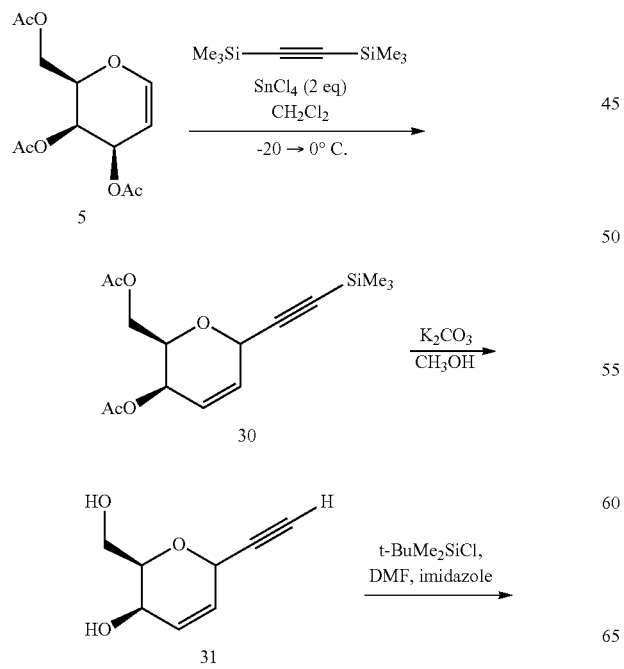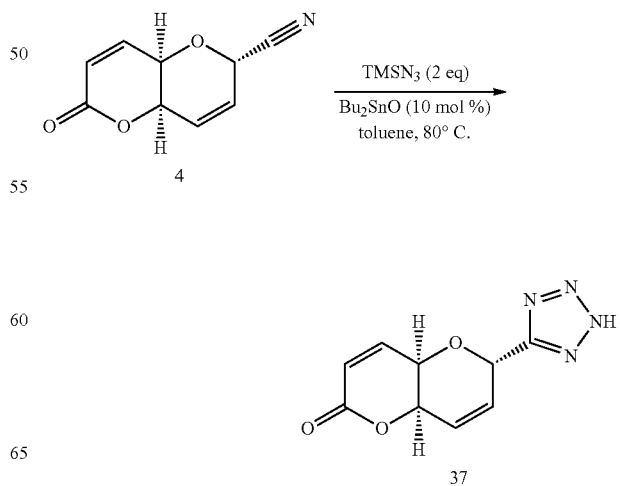

Some of the pyranopyrans synthesized are as follows:

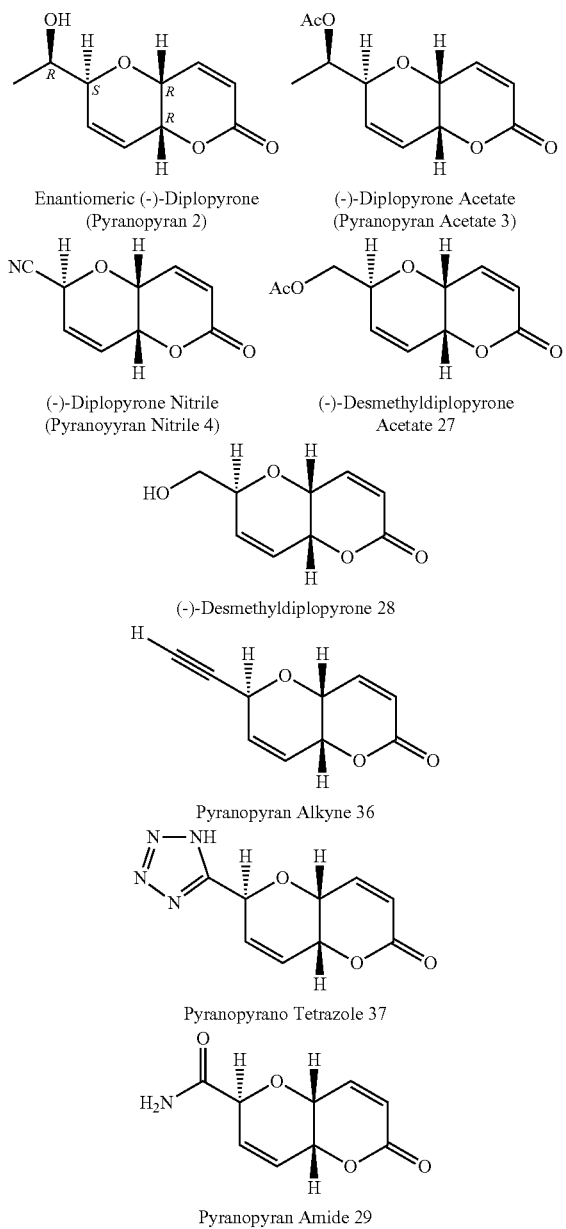

The term "treat," "treating," or "treatment," as used herein, refers to the use of a composition to reduce or prevent a condition, symptom, or disease caused by a pathogen or microbe by (i) preventing the growth of the pathogen or microbe, (ii) inhibiting the growth of the pathogen or microbe, or (ii) substantially killing or eliminating the pathogen or microbe. In addition, the term "treat," "treating," or "treatment" may also refer to the use of a composition to kill, reduce the population of, or inhibit the growth of a microbe or microbial population.

"Microbe" as used herein is synonymous with "microorganism" and may refer to a bacterium, fungus, algae, mold, protozoan, yeast, or other unicellular organism, or a virus.

Other compounds (e.g., a second antimicrobial known in the art) may be added to the composition provided they do not substantially interfere with the intended activity and efficacy of the composition; whether or not a compound interferes with activity and/or efficacy can be determined, for example, by the procedures utilized below.

The terms "object" or "area" as used herein include any place where the presence of microbes (e.g., *Edwardsiella ictaluri, Flavobacterium columnare*) is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, pools, ponds, and so forth; also includes the outer covering of a living being, such as skin, fur, hair, or clothing. Objects treated by the methods described herein include surfaces. Contacting or exposing objects or areas with the antimicrobial composition described herein (to reduce and/or kill microbes) may occur by conventional methods such as spraying or dipping or immersion wherein the object is in contact with the antimicrobial for a certain period of time (e.g., about 120 seconds) or an area is in contact with the antimicrobial for a certain period of time.

"Optional" or "optionally" means that the subsequently described event or circumstance may or may not occur, and that the description includes instances in which said event or circumstance occurs and instances where it does not. For example, the phrase "optionally comprising a second antimicrobial" means that the composition may or may not contain a second antimicrobial and that this description includes compositions that contain and do not contain a second antimicrobial. Also, by example, the phrase "optionally adding a second antimicrobial" means that the method may or may not involve adding a second antimicrobial and that this description includes methods that involve and do not involve adding a second antimicrobial.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

Examples

Melting points were recorded on a Thomas-Hoover apparatus and they are uncorrected. Thin-layer chromatography was carried out on aluminum foil-backed silica gel plates coated with a fluorescent indicator. Plates were developed with cerium molybdate stain. Flash chromatography was carried out using 230-400 mesh silica gel. Optical rotations were recorded on a Perkin-Elmer Model 341 polarimeter. HRMS (High Resolution Mass Spectrometric) analyses were conducted at the University of Illinois Mass Spectrometry Laboratory. NMR spectra were recorded on a Varian (Agilent) Mercury 300 Plus spectrometer in CDCl$_3$ for $^1$H NMR at 300.0 MHz, tetramethysilane reference, δ=0.0 ppm, and, $^{13}$C NMR 70.0 MHz, CDCl$_3$ reference, δ=76.9 ppm. Spectral assignments were confirmed using COSY and DQCOSY experiments. Data were collected on a Brüker-AXS Kappa APEX II CCD diffractometer with 0.71073 Å Mo-Ka radiation. Reagents and starting materials were purchased from Sigma-Aldrich with the exception of 5% Pd/CaCO$_3$ (Alfa Aesar), chlorotitanium triisopropoxide (Strem), and tri-O-acetyl-D-galactal (TCI).

3,4,6-tri-O-acetyl-D-galactal (5) is commercially available (e.g., from Carbosynth Ltd.) and 4,6-di-O-acetyl-2,3-dideoxy-α-D-threo-hexopyranosyl cyanide (6) is make according to the method of Rotella et al. (Rotella, M. R., et al., Carbohydr. Res., 425: 40-42 (2016)).

2,3-Dideoxy-α-D-threo-hex-2-enopyranosyl cyanide (7)

To a solution of diester (6) (365 mg (1.5 mmol) in methanol (15 mL)) was added p-toluenesulfonic acid monohydrate (16 mg, 0.085 mmol). The mixture was stirred under reflux for 7 h and monitored by TLC (50% ethyl acetate/hexanes) until starting material was consumed (R$_f$=0, 50% ethyl acetate/hexanes). The reaction mixture was concentrated to a small volume (2-3 mL) and cooled to −20° C. to give crystalline diol 7 (120 mg, 52%); mp 134-137° C.; lit mp 134-135° C.; [α]$_D^{20}$ −351.30 (c 0.97, EtOH); lit [α]$_D^{21}$ −362.4° (c 1.0, EtOH). HRMS (ESI): m/z calcd for C$_7$H$_9$NO$_3$ [M+Na]$^+$: 178.0480. Found 178.0486. Larger scale deacylation of diester (6) (10.9 g, 45.8 mmol) was carried out by the same procedure in anhydrous methanol (140 mL) with p-toluenesulfonic acid monohydrate (430 mg, 2.3 mmol, 5 mol %) to afford crude diol 7 (6.91 g 97%) as an amorphous solid after concentration of the reaction mixture and drying. This product was entirely suitable for use without further purification in the silylation step.

4,6-di-O-tert-butyldimethylsilyl-2,3-dideoxy-α-D-threo-hex-2-enopyranosyl cyanide (8)

To a stirring solution of diol nitrile (7) (6.13 g, 39.5 mmol) in anhydrous DMF (15 mL) was added imidazole (13.5 g, 198 mmol, 5 eq) and tert-butyldimethylsilyl chloride (15.7 g, 104 mmol, 2.6 eq). The reaction was stirred at rt 12 h then quenched with saturated aq NH$_4$Cl solution and extracted with ethyl acetate (3×30 mL). The combined organic extracts were washed with water (2×20 mL), brine (20 mL), then dried (Na$_2$SO$_4$) and concentrated to a syrup that was purified by flash chromatography with 5% ethyl acetate/hexanes to give 14.3 g (94%) of ether (8) as an oil. R$_f$=0.79 (20% ethyl acetate/hexanes); mp 31-33° C.; [α]$_D^{20}$ −181.2° (c 0.96, CH$_2$Cl$_2$); $^1$H NMR (CDCl$_3$): δ 6.12 (ddd, 1H, J$_{2,3}$=10.0, J$_{3,4}$=5.4, J$_{1,3}$=2.0 Hz, H-3), 5.84 (dd, 1H, J$_{2,3}$=10.0, J$_{1,2}$=3.8 Hz, H-2), 5.08 (dd, 1H, J$_{1,2}$=3.8, J$_{1,3}$=2.1 Hz, H-1), 4.03 (dd, 1H, J$_{3,4}$=5.4, J$_{4,5}$=1.9 Hz, H-4), 3.86-3.70 (m, 3H, H-5,6,6'), 0.90, (t-BuMe$_2$Si), 0.89 (t-Bu Me$_2$Si), 0.08 (t-BuMe$_2$Si), 0.07 (t-BuMe$_2$Si); $^{13}$C NMR (CDCl$_3$): δ 130.40, 123.49, 115.91, 76.78, 62.68, 61.87, 61.24, 25.80, 25.68, 18.20, −4.12, −4.80, −5.24, −5.34. HRMS (CI): m/z calcd for C$_{19}$H$_{38}$NO$_3$Si [M+H]$^+$: 384.2390. Found 384.2389.

4-O-tert-butyldimethylsilyl-2,3-dideoxy-α-D-threo-hex-2-enopyranosyl cyanide (9) and (2S,5R,6S)-5-(tert-butyldimethylsilyl)oxy)-6-formyl-5,6-dihydro-2H-pyran-2-carbonitrile (10)

A mixture of di-O-TBS (tert-butyldimethylsilyl) ether (8) (1.40 g, 3.65 mmol) and pyridinium p-toluenesulfonate PPTS (185 mg, 0.74 mmol, 20 mol %) in anhydrous methanol (20 mL) was stirred at rt for 10 h, until TLC showed consumption of the starting material. The reaction mixture was concentrated rapidly under reduced pressure using a high vacuum pump connected to a rotary evaporator without heating and the resulting oil diluted with dichloromethane (45 mL) and washed with cold water (15 mL), cold saturated aq NaHCO$_3$ solution (10 mL), dried (Na$_2$SO$_4$) and concentrated to yield 800 mg (81%) alcohol (9) as an oil. R$_f$=0.60 (25% ethyl acetate/hexanes); HRMS (CI): m/z calcd for C$_{13}$H$_{24}$NO$_3$Si [M+H]$^+$: 270.1525. Found 270.1533. The crude product alcohol (630 mg, 2.34 mmol) was dissolved in anhydrous dichloromethane (5 mL) and to this solution was added anhydrous dimethyl sulfoxide (DMSO) (2.0 mL, 2.2 g, 28 mmol, 12 eq), and diisopropylethylamine (2.5 mL, 1.9 g, 14 mmol, 6 eq). The mixture was cooled to 0° C. and SO$_3$*pyridine (1.86 g, 11.7 mmol, 5 eq) was added and the reaction stirred for 2 h. Water (30 mL) was added and the mixture was extracted with ethyl acetate (3×20 mL). The combined extracts were washed with water (4×10 mL), brine (10 mL), dried (Na$_2$SO$_4$), and concentrated under reduced pressure. Flash chromatography (16% ethyl acetate/hexanes) gave 540 mg (86%) of aldehyde (10) as an oil. $R_f$=0.70 (25% ethyl acetate/hexanes); $[\alpha]_D^{20}$ −282° (c 1.1, CHCl$_3$); $^1$H NMR (CDCl$_3$): δ 9.61 (s, 1H, CHO), 6.15 (ddd, 1H, $J_{2,3}$=10.1, $J_{3,4}$=5.1, $J_{1,3}$=2.1 Hz, H-3), 5.93 (ddd, 1H, $J_{2,3}$=10.1, $J_{1,2}$=3.7, $J_{2,4}$=0.7 Hz, H-2), 5.28 (dd, 1H, $J_{1,2}$=3.5, $J_{1,3}$=1.9 Hz, H-1), 4.45 (ddd, 1H, $J_{3,4}$=5.3, $J_{4,5}$=3.0, J=0.6 Hz, H-4), 4.30 (d, 1H, $J_{4,5}$=2.9 Hz, H-5), 0.84 ( t-BuMe$_2$Si), 0.08 (t-BuMe$_2$Si); $^{13}$C NMR (CDCl$_3$): δ 198.44, 129.42, 123.47, 115.15, 79.37, 62.28, 62.06, 25.52, 17.92, −4.20, −5.02. HRMS (ESI): m/z calcd for C$_{13}$H$_{21}$NO$_3$SiNa [M+Na]$^+$: 290.1188. Found 290.1194.

Ethyl (Z)-3-((2R,3R,6S)-3-((tert-butyldimethylsilyl)oxy)-6-cyano-3,6-dihydro-2H-pyran-2-yl)acrylate (11)

To a stirring solution of aldehyde (10) (402 mg, 1.5 mmol) in anhydrous methanol (25 mL) at 0° C. was added (carbethoxymethylene)-triphenylphosphorane (651 mg, 1.86 mmol, 1.5 eq) and the reaction was stirred 3 h. Concentration of the mixture and flash chromatography (5% ethyl acetate/hexanes) gave 310 mg (61%) of cis ester (11) as a colorless oil. $R_f$=0.64 (10% ethyl acetate/hexanes); $[\alpha]_D^{20}$ −194° (c 1.8, CHCl$_3$); $^1$H NMR (CDCl$_3$): δ 6.22 (dd, 1H, $J_{6,7}$=11.9, $J_{5,6}$=6.8 Hz, H-6), H-6, 6.13 (ddd, 1H, $J_{2,3}$=10.4, $J_{3,4}$=5.4, $J_{1,3}$=2.1 Hz, H-3), 5.93 (dd, 1H, $J_{6,7}$=11.8, $J_{5,7}$=1.4 Hz, H-7), 5.87 (ddd, 1H, $J_{2,3}$=10.1, $J_{1,2}$=4.0, $J_{2,4}$=0.6 Hz, H-2), 5.36 (ddd, 1H, $J_{5,6}$=6.7, $J_{4,5}$=2.5, $J_{5,7}$=1.7 Hz, H-5), 5.12 (dd, 1H, $J_{1,2}$=3.9, $J_{1,3}$=2.1 Hz, H-1), 4.37 (dd, 1H, $J_{3,4}$=5.4, $J_{4,5}$=2.5 Hz, H-4), 4.20 (q, 2H, J=7.2 Hz), 1.30 (t, 3H, J=7.2 Hz), 0.85 (t-BuMe$_2$Si), 0.018 (t-BuMe$_2$Si), 0.012 (t-BuMe$_2$Si); $^{13}$C NMR (CDCl$_3$): δ 165.30, 145.64, 130.63, 122.82, 120.59, 115.90, 73.86, 62.98, 62.20, 25.71, 18.10, 14.17, −4.34, −4.85. HRMS (ESI): m/z calcd for C$_{17}$H$_{27}$NO$_4$SiNa [M+Na]$^+$: 360.1607. Found 360.1615.

(4aR,6S,8aR)-6-Cyano-6,8a-dihydropyrano-[3,2-b]pyran-2(4aH)-one (Diplopyrone nitrile 4)

Ester (11) (130 mg, 0.385 mol) and TsOH (11 mg, 15 mol %) were stirred under reflux in anhydrous methanol (10 mL) for 4.5 h. The mixture was then concentrated under reduced pressure and dried briefly under vacuum to remove trace methanol. Toluene (10 mL) was added and the mixture stirred overnight under reflux. The crude product was purified by flash chromatography (30% ethyl acetate/hexanes) to give 60 mg (88%, 34% overall from 6) of crystalline nitrile pyranopyran (4). $R_f$=0.23 (30% ethyl acetate/hexanes); mp 162-164° C.; $[\alpha]_D^{20}$ −142° (c 1.0 CHCl$_3$); $^1$H NMR (CDCl$_3$): δ 6.91 (dd, 1H, $J_{3,4}$=9.8, $J_{4,4a}$=5.8 Hz, H-4), 6.33 (m, 1H, H-8), 6.31 (dd, 1H, $J_{3,4}$=9.8, $J_{3,4a}$=0.6 Hz, H-3), 6.17 (ddd, 1H, $J_{7,8}$=10.1, $J_{6,7}$=4.0, $J_{6,8}$=0.8 Hz, H-7), 5.18 (ddd, 1H, $J_{6,7}$=4.1, $J_{6,8}$=2.0, J=0.5 Hz, H-6), 4.74 (dd, 1H, $J_{8,8a}$=5.3, $J_{4a,8a}$=3.0 Hz, H-8a), 4.45 (ddd, 1H, $J_{4,4a}$=5.8, $J_{4a,8a}$=2.9, $J_{4a,8}$=0.5 Hz, H-4a); $^{13}$C NMR (CDCl$_3$): □ 161.29, 138.26, 126.56, 125.56, 124.99, 114.87, 67.46, 62.69, 62.28. HRMS (ESI): m/z calcd for C$_9$H$_7$NO$_3$: 177.0426. Found 177.0431.

1,2;3,4-di-O-isopropylidene-α-D-galacto-1,6-dialdohexopyranose (13)

A mixture of 1,2:3,4-diisopropylidene-α-D-galactopyranose (12) (14.99 g, 57.6 mmol) and 2,2,6,6-tetramethyl-1-piperidinyloxy TEMPO (900 mg, 5.76 mmol, 10 mol %) was stirred in dichloromethane (62 mL, anhydrous) at room temperature as diacetoxyiodobenzene (BAIB) (20.42 g, 63.4 mmol, 1.1 eq) was added to the reaction mixture. After several minutes of stirring, all the BAIB dissolved in the clear, bright orange reaction mixture. After stirring 4 h the reaction mixture was diluted with dichloromethane (35 mL), washed with saturated aq Na$_2$S$_2$O$_3$ (100 mL), and the aqueous layer was extracted with dichloromethane (4×50 mL). The combined organic layers were then washed with saturated aq NaHCO$_3$ sol'n (100 mL) followed by brine (100 mL), dried via sodium sulfate (anhydrous) and concentrated via rotary evaporation to yield a bright orange liquid that was purified by flash chromatography (40:60 ethyl acetate/hexanes) yielding 10.99 (74%) of (13) as a bright yellow oil that was stored at −23° C. $R_f$=0.67 (1:1 ethyl acetate/hexanes). The $^1$H NMR spectra of 1,2:3,4-di-O-aldehyde (13) matched that reported (Brunjes, M., et al., Adv. Synth. Catal., 345: 635-642 (2003)).

7-Deoxy-1,2;3,4-di-O-isopropylidene-D-glycero-α-D-galacto-heptopyranose (14)

In a nitrogen glove box, chlorotitanium triisopropoxide (83 g, 318.1 mmol, 6.2 eq) was added to a Schlenk flask equipped with a Teflon™ plug and a magnetic stir bar. The Schlenk flask was fitted with an addition funnel, sealed with a rubber septum, and removed from the glove box. The Schlenk flask was then connected to a Schlenk line, and the flask was placed under argon. Diethyl ether (220 mL, anhydrous) was added to the flask via a cannula transfer. The mixture was stirred at room temperature until all the solids dissolved, then the reaction mixture was cooled to −50° C. (CO$_{2(s)}$/acetone bath). Methyllithium (199 mL, 1.6 M in diethyl ether, 318.1 mmol, 6.2 eq) was added to the dropping funnel via cannula transfer. The methyllithium was then added to the reaction mixture at a rate so that the cooling bath temperature did not rise above −50° C. Following this addition, the light-yellow reaction mixture was stirred for 1 h (the reaction warmed to −25° C. during this time) and a white precipitate formed. Under an argon counter flow, the addition funnel was replaced with a rubber septum. While maintaining the cooling bath temperature at −25° C., the diethyl ether was removed in vacuo (using the Schlenk line, with a liquid nitrogen cooled trap to collect solvent). When the solvent was removed, the methyl(triisopropoxy)titanium thus formed was kept under argon.

Methyl(triisopropoxy)titanium was suspended in dichloromethane (220 mL, anhydrous), and the Schlenk flask was cooled to −78° C. (CO$_2$/acetone bath). A solution of 1,2:3,4-di-O-aldehyde (13) (13.24 g, 51.3 mmol) in dichloromethane (50 mL, anhydrous) was added dropwise via a syringe while maintaining a cooling bath temperature of −78° C. The reaction mixture was allowed to slowly warm over 22 h under argon (a needle was affixed to an argon balloon and was inserted through the septum of the Schlenk flask in order to prevent pressure build up). At this point, the cooling bath reached 20° C. The reaction mixture was quenched via the addition of water. The first 10 mL of water was added dropwise until vigorous effervescence subsided. Following this, an additional 240 mL of water was added to the reaction mixture followed by 300 mL of diethyl ether. The entire mixture (including solids formed) was transferred into an Erlenmeyer flask and stirred vigorously for 20 min. After filtration, the solids were washed with diethyl ether (200 mL), the filtrate was transferred to a separatory funnel, the organic and aqueous layers were separated, and the aqueous phase was extracted with diethyl ether (2×200 mL). The combined organic extracts were washed successively with H₂O (250 mL), brine (400 mL), dried via MgSO₄ (anhydrous) and concentrated to yield 10.36 g (78%) of a bright yellow oil that was filtered through a pad of SiO₂, washed with diethyl ether (300 mL), and concentrated under reduced pressure to yield 10.34 g (74%) of 1,2;3,4-di-O-isopropylidene-7-deoxy-D-glycero-D-galacto-hepto-heptopyranoside (14) as a pale yellow oil that was stored at −23° C. $R_f$=0.45 (1:1 ethyl acetate/hexanes) and used without further purification. The $^1$H NMR spectrum matched that reported,[37] except for the presence of the minor β-L-glycero diastereomer that was seen previously (19:1 dr) but in this larger-scale preparation was estimated at approximately 0.7%.

1,2,3,4,6-Penta-O-acetyl-7-deoxy-D-glycero-D-galacto-heptopyranoside (15)

A mixture of 1,2;3,4-di-O-isopropylidene-7-deoxy-D-glycero-D-galacto-heptopyranoside (14) (10.30 g, 37.55 mmol) and acetic acid/water (80 mL, 60% v/v) was heated and stirred under reflux. As the reaction progressed the reaction mixture became dark brown in color. After 2 h, TLC analysis (1:1 ethyl acetate/hexanes) showed the disappearance of starting material and the reaction mixture was allowed to cool to room temperature. Once cooled the solvent was removed under reduced pressure (vacuum pump) at a temperature no greater than 30° C. The resulting brown oil was taken up in ethanol (anhydrous), concentrated under reduced pressure, and dried under high vacuum. The crude material was dissolved in pyridine (150 mL, anhydrous) and cooled to 0° C. Acetic anhydride (110 mL) was added via syringe. After five minutes of stirring at 0° C., the reaction mixture was allowed to warm to room temperature and stirred 22 h. The reaction was quenched by the addition of 110 mL of H₂O and stirred for 10 minutes. Following this, the reaction mixture was taken up in 100 mL of dichloromethane and the organic and aqueous layers were separated. The aqueous layer was extracted with dichloromethane (4×100 mL). The combined organic layers were washed with saturated aq CuSO₄ solution (4×500 mL), saturated aq NaHCO₃ sol'n (250 mL), brine (250 mL), dried (Na₂SO₄), and concentrated under reduced pressure to yield 13.5 g (89%) of (15) as a foam in a 1:1.3 mixture of α/β anomers that was stored at 0° C. $R_f$=0.46 (1:1 ethyl acetate/hexanes). The $^1$H NMR spectrum of 1,2,3,4,6-Penta-O-acetyl-7-deoxy-D-glycero-α/β-D-galacto-heptopyranoside (15) matched that reported (Grabowski, U., et al., Carbohydr. Res., 305: 351-361 (1998)). $^{13}$C NMR (CDCl₃): δ 170.32, 170.29, 170.15, 170.00, 169.91, 169.74, 169.68, 169.37, 169.04, 168.89, 92.42, 92.42, 89.72, 77.23, 76.21, 73.12, 70.85, 67.75, 66.21, 65.90, 20.91, 20.87, 20.82, 20.67, 20.58, 17.49. HRMS (ESI): m/z calcd for C₁₇H₂₄O₁₁ [M+Na]⁺=427.1216. Found 427.1227.

2,3,4,6-Tetra-O-acetyl-7-deoxy-D-glycero-α-D-galacto-heptopyranoside bromide (16)

1,2,3,4,6-Penta-O-acetyl-7-deoxy-D-glycero-α/β-D-galacto-heptopyranoside (15) (13.45 g, 33.26 mmol) was cooled to 0° C. then dissolved in 33% wt HBr solution in glacial acetic acid (75 mL). The dark brown reaction mixture was allowed to stir at 0° C. for 5 min. Following this the reaction mixture was allowed to warm to room temperature. After 3 h, TLC analysis (1:1 ethyl acetate/hexanes) showed the disappearance of starting material, the reaction mixture was taken up in dichloromethane (250 mL) and washed with ice water (200 mL). The aqueous layer was extracted with dichloromethane (2×200 mL), the combined organic layers were washed with cold water until the washings were neutral (4×500 mL), dried (Na₂SO₄), and concentrated via reduced pressure to 12.01 g (85%) of glycosyl bromide (16) as a foam that was stored at −23° C. $R_f$=0.63 (1:1 ethyl acetate/hexanes); [α]$_D$+197.8° (c 1.4, CHCl₃); $^1$H NMR (CDCl₃): δ 6.66 (d, 1H, $J_{1,2}$=3.97 Hz, H-1), 5.54 (dd, 1H, $J_{5,6}$=9.38, $J_{5,4}$=1.23 Hz, H-4), 5.39 (dd, 1H, $J_{3,4}$=3.29, $J_{3,2}$=10.63 Hz, H-3), 5.02 (dq, 1H, $J_{6,7}$=6.24, $J_{6,5}$=9.38 Hz, H-6), 5.02 (dd, 1H, $J_{2,3}$=10.63, $J_{2,7}$=6.24 Hz, H-2), 4.12 (ddd, 1H, $J_{5,6}$=9.38 Hz, H-5), 2.11, 2.10, 2.00, 1.99 (4s, 12H, OCOCH₃), 1.26 (d, 3H, $J_{7,6}$=6.24, CH₃), $^{13}$C NMR (CDCl₃): δ 169.99, 169.69, 88.28, 75.05, 67.94, 67.77, 65.85, 65.73, 53.45, 20.83, 20.68, 20.51, 20.45, 17.28. HRMS (ESI): m/z calcd for C₁₅H₂₁O₉Br [M+Na]⁺=447.0267. Found 447.0274.

2,3,4,6-Tetra-O-acetyl-7-deoxy-1,5-anhydro-D-gluco-hept-1-enitol (17)

A mixture of glycosyl bromide (16) (11.87 g, 27.70 mmol) and tetra-n-butylammonium bromide (8.93, 27.7 mmol, 1 eq) was stirred in acetonitrile (6 mL, anhydrous) as 1,8-diazabicyclo[5.4.0]undec-7-ene (DBU) (11.15 mL, 76.2 mmol, 2.75 eq) was added via a syringe. Immediately following the addition of DBU the reaction became black. After 20 min TLC analysis (1:1 ethyl acetate/hexanes) showed the disappearance of starting material and the reaction mixture was diluted with 6 mL of dichloromethane and concentrated via rotary evaporation. The resulting syrup was taken up in dichloromethane (150 mL) and washed with 10% HCl (150 mL), followed by saturated NaHCO₃ (150 mL), dried (Na₂SO₄), and concentrated via rotary evaporation to yield a dark oil that was purified by flash chromatography (1:1 ethyl acetate/hexanes) to yield 6.94 g (73%) of glycal (17) as a yellow oil that was stored at 0° C. $R_f$=0.50 (1:1 ethyl acetate/hexanes); [α]$_D$ +57.7 (c 1.3, CHCl₃); $^1$H NMR (300 MHz, CDCl₃): δ 6.63 (d, 1H, $J_{1,3}$=1.75 Hz, H-1), 5.89 (ddd, 1H, $J_{3,4}$=5.04, $J_{3,1}$=1.75 Hz, H-3), 5.53 (dd, 1H, $J_{4,3}$=5.04, $J_{4,5}$=0.95 Hz, H-4), 5.02 (dq, 1H, $J_{6,7}$=6.25, $J_{6,5}$=9.15 Hz, H-6), 3.99 (ddd, 1H, $J_{5,6}$=9.15 Hz, H-5), 2.11, 2.02, 2.01, (3s, 12H, OCOCH₃), 1.32 (d, 3H, $J_{7,6}$=6.25, CH₃); $^{13}$C NMR (CDCl₃): δ 170.29, 169.86, 169.75, 169.36, 138.76, 127.34, 77.55, 66.38, 63.96, 62.10, 20.94, 20.53, 20.36, 17.16. HRMS (ESI): m/z calcd for C₁₅H₂₀O₉[M+Na]⁺=367.1005. Found 367.1005.

(R)-1-((2S,5R,6R)-5-Hydroxy-6-((trimethylsilyl) ethynyl)-5,6-dihydro-2H-pyran-2-yl)ethyl acetate (18)

A homogeneous mixture of glycal (17) (1.9 g, 5.52 mmol) and bis(trimethylsilyl)acetylene (3.76 g, 22.1 mmol, 4 eq) in dichloromethane (25 mL, anhydrous) was degassed and place under argon. The reaction mixture was cooled to −20° C. (CO₂/acetone) and SnCl₄ (22.1 mL, 1 M in dichloromethane, 4 eq) was added via syringe. Following this addition, the reaction mixture was stored at 0° C. After 70 h, TLC analysis showed the disappearance of starting material, and the reaction mixture was poured into a 1:1 mixture of saturated aq NaHCO₃/Na, K tartrate solution (100 mL) and stirred for 30 min at 0° C. After several minutes of stirring the reaction mixture became an orange/brown color. After 30 min, the reaction mixture was taken up in dichloromethane, and the organic and aqueous layers were separated. The aqueous layer was extracted with dichloromethane (4×100 mL) and the combined organic layers were washed with brine (200 mL), dried (MgSO₄), and concentrated via rotary evaporation to yield alkynyl glycoside (18) as a light-yellow oil. To the crude product was added methanol (30 mL) and cerium(III)chloride heptahydrate (3.08 g, 8.28 mmol, 1.5 eq) to give an orange/brown homogeneous mixture that was cooled to 0° C. Once cooled, NaBH$_4$ (0.313 g. 8.28 mmol, 1.5 eq) was added to the reaction mixture portion-wise over 5 minutes. After 1 h 40 min, TLC analysis showed the disappearance of starting material and the reaction mixture was quenched by the addition of 15 mL of ice cold H$_2$O. After 10 min of stirring, the methanol was removed via rotary evaporation at a temperature no greater than 35° C. The resulting faint orange aqueous solution was filtered through cotton and extracted with dichloromethane (4×100 mL). The combined organic extracts were then washed with brine (200 mL), dried (Na$_2$SO$_4$), and concentrated under rotary evaporation to yield 1.37 g (88%) a yellow/orange liquid that crystallized overnight at 0° C. R$_f$=0.69 (1:1 ethyl acetate/hexanes); mp 44.5° C.-46.0° C.; [α]$_D$ −28.6° (c 1.4, CHCl$_3$); $^1$H NMR (300 MHz, CDCl$_3$): δ 5.82 (ddd, 1H, J$_{3,5}$=2.00, J$_{3,4}$=10.51, J$_{3,2}$=2.05, J$_{3,1}$=0.80, Hz, H-3), 5.74 (dt, 1H, J$_{4,5}$=1.71, J$_{4,3}$=10.51, J$_{4,2}$=1.64 Hz, H-4), 4.96 (dq, 1H, J$_{6,7}$=6.41, J$_{6,5}$=4.34 Hz, H-6), 4.90 (d, 1H, J$_{1,3}$=0.80, J$_{1,2}$=5.84 Hz, H-1), 4.25 (bs, 1H, J$_{2,3}$=2.05, J$_{2,1}$=5.84 Hz, H-2), 2.08 (s, 3H, OCOCH$_3$), 1.85 (bs, 1H, OH), 1.21 (d, 3H, J$_{7,6}$=6.41 Hz, CH$_3$), 0.18 (s, 9H, SiMe$_3$); $^{13}$C NMR (CDCl$_3$): δ 170.45, 129.41, 127.04, 99.23, 94.34, 72.00, 71.45, 67.92, 63.50, 21.29, 14.91, −0.184. HRMS (ESI): m/z calcd for C$_{14}$H$_{22}$O$_4$Si [M+Na]$^+$=305.1185. Found 305.1190.

(R)-1-((2S,5R,6R)-5-Hydroxy-6-ethynyl)-5,6-dihydro-2H-pyran-2-yl)ethyl acetate (19)

To a stirring solution of alkynyl glycoside (18) (3.0 g, 10.6 mmol) in tetrahydrofuran (THF) (10 mL) at 0° C. was added tetrabutylammonium fluoride TBAF (3.18 mL, 1 M in THF, 0.3 eq) via syringe. After 15 min TLC analysis (1:1 ethyl acetate/hexanes) showed the disappearance of starting material. The THF was removed via rotary evaporation to yield a brown oil. This crude material was purified by flash chromatography (1:1 ethyl acetate/hexanes) to yield 1.52 g (68%) of alkyne (19) as a faint yellow oil that was stored at −23° C. R$_f$=0.41 (1:1 ethyl acetate/hexanes); [α]$_D$ −47.8° (c 1.0, CHCl$_3$); $^1$H NMR (300 MHz, CDCl$_3$): δ 5.77 (ddd, 2H, J$_{4,5}$=1.73, J$_{4,3}$=10.72 Hz, H-3, H-4), 4.97 (dq, 1H, J$_{6,7}$=6.55, J$_{6,5}$=4.34 Hz, H-6), 4.93 (dd, 1H, J$_{1,3}$=0.78, J$_{1,2}$=5.8 Hz, H-1), 4.43 (cm, 1H, J$_{5,6}$=4.34, J$_{5,4}$=1.7, J$_{5,3}$=2.3, J$_{5,1}$=0.63 Hz, H-5), 4.43 (dddt, 1H, J$_{2,4}$=1.7, J$_{2,3}$=1.7, J$_{2,2-OH}$=11.0 J$_{2,1}$=5.8 Hz, H-2), 2.49 (d, 1H, J$_{CH,1}$=2.24 Hz, CH), 2.08 (s, 3H, OCOCH$_3$), 1.89 (d, J$_{OH,2}$=11.0 Hz, OH), 1.22 (d, 3H, J$_{7,6}$=6.55 Hz, CH$_3$); $^{13}$C NMR (CDCl$_3$): δ 170.51, 129.37, 126.97, 78.08, 76.48, 72.07, 71.37, 67.28, 63.62, 21.73, 14.79. HRMS (ESI): m/z calcd for C$_{11}$H$_{14}$O$_4$ [M+Na]$^+$=233.0790. Found 233.0793.

(R)-1-((2S,5R,6R)-5-Hydroxy-6-vinyl-5,6-dihydro-2H-pyran-2-yl)ethyl acetate (20)

A heterogeneous mixture of 5% Pd/CaCO$_3$ (10 mg) and quinoline (23 μL, 0.19 mmol, 0.58 eq) was stirred in ethyl acetate (10 mL) at 0° C. as the reaction vessel was purged with hydrogen gas for 20 min. Alkyne (19) (70 mg, 0.33 mmol) was added to the reaction mixture in a solution of ethyl acetate (10 mL). The reaction mixture was purged with hydrogen and stirred 65 min, filtered through a pad of Celite®, washed with ethyl acetate, and concentrated under reduced pressure to yield 50 mg (71%) of vinyl glycoside (20) a colorless oil that was stored at 0° C. R$_f$=0.41 (1:1 ethyl acetate/hexanes); [α]$_D$ −186.6° (c 0.98, CHCl$_3$), $^1$H NMR (CDCl$_3$, 300 MHz): δ 6.10 (ddd, J$_{3,2}$=4.7, J$_{3,4}$=10.4, J$_{3,5}$=2.3 Hz, H-3), 5.97 (ddd, J$_{1',1}$=6.0, J$_{1',2'e}$=17.3, J$_{1',2'z}$=10.5 Hz, H-1'), 5.90 (ddd, J$_{4,3}$=10.4, J$_{4,5}$=2.3 Hz, H-4), 5.43 (dt, J$_{2e',1}$=17.3, J$_{2'e,2'z}$=1.6 Hz, H-2'e), 5.35 (dt, J$_{2'z,1}$=10.5, J$_{2'z,2'e}$=1.6 Hz, H-2'z), 5.04 (pent, J$_{6,5}$=7.2, J$_{6,7}$=6.5 Hz, H-6), 4.33 (cm, J$_{1,2}$=2.9, J$_{1,1'}$=6.0, J$_{1,2'z}$=1.2, J$_{1,2'e}$=1.2 Hz, H-1), 4.18 (cm, J$_{5,3}$=2.3, J$_{5,4}$=3.0 Hz, H-5), 3.97 (bs, 1H, H-2), 2.06 (s, OCOCH$_3$), 1.70 (d, J$_{OH,2}$=11.51 Hz, OH) 1.30 (d, J$_{7,6}$=6.5 Hz, CH$_3$); $^{13}$C NMR (CDCl$_3$): δ 170.35, 133.87, 128.59, 128.42, 118.72, 74.62, 73.80, 71.04, 63.76, 21.27, 16.84. HRMS (ESI): m/z calcd for C$_{11}$H$_{16}$O$_4$[M+Na]$^+$=235.0946. Found 235.0941.

(2S,3R,6S)-6-((R)-1-acetoxyethyl)2-vinyl-3,6-dihydro-2H-pyran-2-yl)ethyl acrylate (21)

A pale yellow, homogeneous mixture of vinyl glycoside (20) (1.01 g, 4.76 mmol), acryloyl chloride (0.94 mL, 11.45 mmol, 2.4 eq), and triethylamine (2.5 mL, 19.1 mmol, 4 eq) was stirred in dichloromethane (10 mL) at 0° C. After 10 min TLC analysis (1:1 ethyl acetate/hexanes) showed the disappearance of starting material. The reaction mixture was taken up in dichloromethane (40 mL) and washed with cold saturated aq NaHCO$_3$ solution (25 mL), dried (Na$_2$SO$_4$) and concentrated under reduced pressure to give a yellow solid that was purified by flash chromatography (30:70 ethyl acetate/hexanes) to yield 870 mg (69%) of compound (21) as a colorless oil that was stored at −23° C. R$_f$=0.67 (1:1 ethyl acetate/hexanes); [α]$_D$ −207.5° (c 1.0, CHCl$_3$); $^1$H NMR (CDCl$_3$, 300 MHz): δ 6.41 (dd, J$_{2''e,1''}$=17.4, J$_{2''e,2''z}$=1.5 Hz, H-2''e), 6.39 (dt, J$_{2'e,1}$=ND J$_{2'e,2'z}$=ND, H-2'e), 6.27 (dt, J$_{2'z,1}$=ND, J$_{2'z,2'e}$=ND, H-2'z), 6.11 (dd, J$_{1'',2''e}$=17.4, J$_{1'',2''z}$=10.3 Hz, H-1''), 6.03 (cs, J$_{3,2}$=ND, J$_{3,4}$=ND, J$_{3,5}$=ND, H-3), 6.03 (cs, J$_{4,3}$=ND, J$_{4,5}$=~0, H-4), 5.89 (ddd, J$_{1',1}$=6.3, J$_{1,2'e}$=ND, J$_{1',2'z}$=ND, J$_{1,2'e}$=17.3, J$_{1',2'z}$=9.9 Hz, H-1'), 5.83 (dd, J$_{2''z,1''}$=10.3, J$_{2''z,2''e}$=1.5 Hz, H-2''z), 5.26 (cm, J$_{2,1}$=4.0, H-2), 5.03 (pent, J$_{6,5}$=6.5, J$_{6,7}$=6.4 Hz, H-6), 4.51 (ct, J$_{1,2}$=4.0, J$_{1,1'}$=6.3 Hz, J$_{1,2'z}$=ND, J$_{1,2'e}$=ND, H-1) 4.24 (d, J$_{5,4}$=~0, J$_{5,6}$=7.2 Hz, H-5), 2.06 (s, OCOCH$_3$), 1.30 (d, J$_{7,6}$=6.5 Hz, CH$_3$); $^{13}$C NMR (CDCl$_3$): δ 170.35, 165.63, 132.91, 131.43, 130.15, 128.04, 124.66, 118.98, 73.17, 72.76, 71.13, 65.71, 21.27, 16.45. HRMS (ESI): m/z calcd for C$_{14}$H$_{18}$O$_5$[M+Na]$^+$=289.1052. Found 289.1052.

(4aR,6S,8aR)-6-((R)-1-Acetoxyethyl)-6,8a-dihydropyrano[3,2-b]pyran-2-(4aH)-one (3)

A solution of compound (21) (86 mg, 0.36 mmol) in anhydrous toluene (10 mL) was degassed under argon gas while stirring. Following this, Grubbs II (27 mg, 10 mol %) and phenol (75 mg, 0.8 mmol, 2.5 eq) were added and the reaction mixture was degassed under argon once again and heated to 80° C. After 1 h TLC analysis (1:1 ethyl acetate/hexanes) showed the disappearance of starting compound (21). The reaction mixture was concentrated under reduced pressure to give a dark brown oil that was purified via flash chromatography (1:1 ethyl acetate/hexanes) to yield 45 mg (59%) of (−)-diplopyrone acetate (3) as an oil that crystallized when stored at −23° C. R$_f$=0.33 (1:1 ethyl acetate/hexanes); mp 105-107.5° C.; [α]$_D$=−98.0° (c 1.3, CHCl$_3$); $^1$H NMR (CDCl$_3$, 300 MHz): δ 6.86 (dd, J$_{4,3}$=10.0, J$_{4,4a}$=3.5 Hz, H-4), 6.10 (dd, J$_{3,4}$=10.0, J$_{3,4a}$=1.6 Hz, H-3), 6.05 (cm, J$_{8,7}$=10.5, J$_{8,8a}$=2.5 H, H-8), 6.01 (cm, J$_{7,6}$=2.0, J$_{7,8}$=10.5 Hz, H-7), 5.02 (dq, J$_{9,6}$=5.5, J$_{9,10}$=6.4 Hz, H-9), 4.90 (cd, J$_{7,8}$=ND, J$_{8a, 8}$=2.5, J$_{8a, 4a}$=5.2 Hz, H-8a), 4.75 (ct, $J_{4,\,4a}$=3.5, $J_{4a,\,3}$=1.6, $J_{4a,\,8a}$=5.2 Hz, H-4a), 2.08 (s, OCOCH$_3$), 1.28 (d, $J_{10,9}$=6.4 Hz, CH$_3$); $^{13}$C NMR (CDCl$_3$): δ 170.30, 161.81, 143.51, 129.92, 124.18, 123.60, 73.05, 71.13, 69.54, 64.14, 29.69, 21.26, 15.75. HRMS (ESI): m/z calcd for C$_{12}$H$_{15}$O$_5$ [M+Na]$^+$=239.0919. Found 239.0917.

(4aR,6S,8aR)-6-((R)-1-Hydroxyethyl)-6,8a-dihydro-pyrano[3,2-b]pyran-2-(4aH)-one (2)

A mixture of (−)-diplopyrone acetate (3) (35 mg, 0.15 mmol) was stirred in THF as H$_2$O was added (five drops) followed by lipase PS 30 Amano (~3 eq wt). Not all the lipase dissolved in the reaction mixture. After nine days, the reaction mixture was concentrated under reduced pressure to yield a beige solid that was purified by column chromatography (1:1 ethyl acetate/hexanes followed by ethyl acetate) to yield 18.5 mg (63%, 80% based on recovered (3)) of (2) as a colorless oil that crystallized overnight at −23° C. $R_f$=0.26 (9:1 ethyl acetate/hexanes); mp 73.2-74° C., $[\alpha]_D$=−79.2° (c 0.6, CHCl$_3$); $^1$H NMR (CDCl$_3$, 300 MHz): δ 6.88 (dd, 1H, $J_{4,3}$=10.0, $J_{4,4a}$=2.8 Hz, H-4), 6.07 (dd, 1H, $J_{3,4}$=10.0, $J_{3,4a}$=1.8 Hz, H-3), 6.05 (cm, 1H, $J_{8,7}$=ND, $J_{8,8a}$=2.0 Hz, H-8), 6.01 (cm, 1H, $J_{7,8}$=10.7, $J_{7,8a}$=ND, $J_{7,6}$=1.8 Hz, H-7), 4.97 (cm, 1H, $J_{8,\,8a}$=2.0, $J_{8,7}$=ND, $J_{8a,\,4a}$=5.8 Hz, H-8a), 4.91 (cm, 1H, $J_{4a,8a}$=5.8, $J_{4a,4}$=2.8, $J_{4a,\,3}$=1.8 Hz, H-4a), 4.07 (cm, 1H, $J_{6,9}$=4.1, $J_{6,8}$=3.0, $J_{6,8a}$=ND, $J_{6,7}$=1.8 Hz, H-6), 3.96, (dq, 1H, $J_{9,10}$=6.5, $J_{9,6}$=4.1 Hz, H-9), 1.87 (bs, 1H, OH), 1.24 (d, 3H, $J_{10,9}$=6.5 Hz, CH$_3$), $^{13}$C NMR (CDCl$_3$): δ 161.81, 144.30, 129.63, 124.60, 123.24, 74.79, 70.00, 69.64, 64.84, 18.73. HRMS (ESI): m/z calc for C$_{10}$H$_{13}$O$_4$ [M+H]$^+$=197.0814.

2,3,4,6-Tetra-O-acetyl-1-deoxy-D-arabino-hex-1-enopyranose (22)

Glycal 22 was prepared following the published procedure (Ferrier, R. J., IN: Methods in Carbohydrate Chemistry, VI; R. L. Whistlerand J. N. BeMiller, Eds; Academic Press: New York, 307-311 (1972)) from commercially available 2,3,4,6-tetra-O-acetyl-α-D-glucopyranosyl bromide (20.0 g, 48.6 mmol). Concentration of the crude product gave a red syrup to which a minimum amount of hot isopropanol was added. The solution was cooled to rt then stored at 0° C. and white crystalline product was collected. Two more crops of crystals were isolated from the mother liquor and the combined crystal harvests were dried under high vacuum to afford 12.5 g (77%) of the glycal 22. $R_f$=0.4 (40% ethyl acetate 60% hexanes); mp 60-63° C.; lit mp 61, 65-66° C.; $[\alpha]_D^{23}$ −18° (c 1.0, ethanol); lit $[\alpha]_D$ −20° (c 1.8, ethanol); $^1$H NMR (CDCl$_3$) δ 6.62 (s, 1H), 5.84 (d, 1H, J=4.7 Hz), 5.48 (dd, 1H, J=5.0, 2.0 Hz), 4.42-4.19 (m, 3H), 2.13 (s, 3H), 2.11 (s, 3H), 2.08 (s, 3H), 2.04 (s, 3H); $^{13}$C NMR (CDCl$_3$) δ 170.2, 169.9, 169.3, 169.2, 139.2, 127.4, 74.1, 67.5, 66.3, 60.9, 20.5, 20.5, 20.3.

(2S, 5R, 6R)-5-Hydroxy-6-(trimethylsilyl)ethynyl-5,6-dihydro-2H-pyran-2-yl)methyl acetate (23)

TMS-alkynyl glycoside 23 was prepared from glycal 22 by the method of Chang and Isobe (Chang, W.-C., and M. Isobe, Tetrahedron, 70: 8324-8333 (2014). From 9.0 g (27.2 mmol) of glycal there was obtained 4.20 g (57%) of 23 as an oil after purification by flash chromatography. $R_f$=0.4 (40% ethyl acetate/hexanes; $[\alpha]_D^{23}$ −100.2° (c 1.8, CHCl$_3$); lit $[\alpha]_D^{23}$ −99.20 (c 1.2, CHCl$_3$). The NMR data for 23 matched that previously reported.

(2S,5R,6R)-6-Ethynyl-5-hydroxy-5,6-dihydro-2H-pyran-2-yl-methyl acetate (24)

Adapting the procedure of Yeom et al. (Yeom, C.-E., et al., Synlett, 565-568 (2008)) alkynyl glycoside 23 (730.0 mg, 2.27 mmol) was added to a stirring solution of acetonitrile and deionized water (19:1 v/v) heated to 60° C. Stirring was maintained for 10 minutes then DBU (406 µl, 2.27 mmol, 1 equiv) was added. The reaction was monitored by TLC (1:1 ethyl acetate/hexanes) until complete, usually in 50 min. The crude material was concentrated and the crude product purified by flash chromatography using a gradient elution of 30-40% ethyl acetate/hexanes. Desilylated 24 (430 mg, 80%) was obtained as a white solid. $R_f$=0.18 (40% ethyl acetate 60% hexanes); mp 73-76° C.; $[\alpha]_D^{23}$ −52.4° (c 1.2, CHCl$_3$); $^1$H NMR (CDCl$_3$) δ 5.88 (dd, 1H, J=10.5, 2.3, H-3), 5.75 (dd, J=10.5, 2.0, H-4), 4.90 (dd, 1H, J=5.2, 2.3 Hz, H-1), 4.58 (octet, 1H, H-5), 4.32 (m, 1H, J=10.3, 5.2, 2.3, 2.0 Hz, H-2), 4.14 (d, 2H, J=5.0 Hz, H-6,6'), 2.52 (d, 1H, J=2.3 Hz), 2.09 (s, 3H), 2.00 (d, 1H, J=10.3, OH); $^{13}$C NMR (CDCl$_3$) δ 170.8, 129.5, 127.0, 78.2, 76.4, 69.2, 67.1, 65.0, 63.5, 20.7. HRMS (ESI): calcd for C$_{10}$H$_{12}$O$_4$Na [M+Na]$^+$: 219.0633. Found 219.0631.

(2S,5R,6R)-6-Ethenyl-5-hydroxy-5,6-dihydro-2H-pyran-2-yl-methyl acetate (25)

A 250 ml round-bottom flask fitted with a 2-way adaptor and balloon was charged with ethyl acetate (40 ml), quinoline (222.1 µl, 1.8 mmol, 0.58 equiv), and Lindlar's catalyst (50.0 mg, 10 wt %) and cooled in an ice bath. The mixture was purged three times with hydrogen then stirred 20 min at 0° C. A solution of alkyne 24 (400 mg, 2.6 mmol) in ethyl acetate (30 ml) was added and the flask was again purged three times then stirred at 0° C. The reaction was monitored by TLC until starting material was consumed, typically in 1 to 1.5 h. The mixture was filtered through a pad of Celite® which was washed with ethyl acetate and the filtrate concentrated to give an oil that was purified by flash chromatography (40% ethyl acetate/hexanes). There was obtained 405 mg (97%) of 25 as an oil. $R_f$=0.12 (40% ethyl acetate/hexanes); $[\alpha]_D^{23}$ −112.3° (c 0.9, CHCl$_3$); $^1$H NMR (CDCl$_3$) δ 6.10 (ddd, 1H, J=10.1, 5.1, 2.1 Hz, H-3), 5.92 (ddd, 1H, J=17.4, 10.6, 5.98 Hz, HC=CH$_2$), 5.76 (dd, 1H, J=10.1, 3.1, H-4), 5.36 (dd, 1H, J=17.4, 1.5 Hz, HC=CH$_2$), 5.27 (dd, 1H, J=10.6, 1.5 Hz, HC=CH$_2$), 4.44 (m, 1H, J=8.4, 3.7, 3.1, 2.1 Hz, H-5), 4.33-4.24 (m, 2H, J=11.9, 8.4, 5.9, 1.5 Hz, H-1, H-6), 3.96 (dd, 1H, J=11.9, 3.7, H-6'), 3.85 (m, 1H, H-2), 2.02 (s, 3H, CH$_3$), 1.94 (bs, 1H, OH); $^{13}$C NMR (CDCl$_3$) δ 170.8, 134.2, 129.7, 129.3, 128.2, 128.0, 118.3, 73.8, 73.7, 71.5, 71.1, 63.7, 63.3, 62.9, 62.6, 20.9. HRMS (ESI): calcd for C$_{10}$H$_{14}$O$_4$Na [M+Na]$^+$: 221.0790. Found 219.0790.

(2R,3R,6S)-6-(Acetyloxy)methyl]-2-ethenyl-3,6-dihydro-2H-pyran-3-yl prop-2-enoate (26)

To a stirring solution of vinyl glycoside 25 (167 mg, 0.84 mmol), acryloyl chloride (128 µl, 1.3 mmol) and triethylamine (155 µl, 0.21 mmol 2.5 eq) in anhydrous dichloromethane (5 mL) at 5° C. was added a solution of DMAP (5 mg) in 500 µl of dichloromethane. The reaction was monitored by TLC (30% ethyl acetate/hexanes) and completed in 20 min. The mixture was then diluted with dichloromethane (25 ml) and washed once with sat'd aq NaHCO$_3$ sol'n, dried (Na$_2$SO$_4$) and concentrated to an oil that was purified by flash chromatography using 30% ethyl acetate/ hexanes. There was obtained 185 mg, (88%) of acryloyl derivative 26. $R_f$=0.46 (40% ethyl acetate/hexanes); $[\alpha]_D^{23}$ −292° (c 1.0, CHCl$_3$); $^1$H NMR (CDCl$_3$) δ 6.78 (dd, 1H, J=10.4, 1.5 Hz, HC=CH$_2$), 6.36, (dd, 1H, J=17.3, 1.5 Hz, HC=CH$_2$), 6.06, (ddd, 1H, J=17.3, 10.4 Hz, HC=CH$_2$), 6.04 (ddd, 1H, J=10.6, 4.6, 2.3 Hz, H-3), 5.91 (ddd, 1H, J=10.3, 2,8, 1.0 Hz, H-4), 5.81 (ddd, 1H, J=17.5, 10.7, 5.6 Hz, HC=CH$_2$), 5.33 (dt, 1H, J=17.4, 1.3, Hz, HC=CH$_2$), 5.20 (dt, 1H, J=10.7, 1.3 Hz, HC=CH$_2$), 5.13 (m, J=4.6, 3.0, 1.0 Hz, H-2), 4.47 (m, 2H, J=7.6, 5.6, 4.0, 3.0, 2.8, 2.3, 1.3 Hz, H-1, H-5), 4.30 (dd, 1H, J=10.9, 7.6 Hz, H-6), 3.98, (dd, H, J=10.9, 4.0 Hz, H-6'), 2.02 (s, 3H, CH$_3$); $^{13}$C NMR (CDCl$_3$) δ 170.6, 165.6, 133.1, 131.2, 130.1, 128.1, 125.2, 118.4, 72.0, 70.6, 65.5, 63.5, 20.7. HRMS (ESI): calcd for C$_{13}$H$_{16}$O$_5$Na [M+Na]$^+$: 275.0895. Found 275.0891.

(2S,4aR,8aR)-6-Oxo-2,4a,6,8a-tetrahydropyrano[3,2-b]pyran-2-yl]methyl acetate (27)

A flame-dried 50 ml 3-neck round bottom flask equipped with a reflux condenser and septum was flushed with argon and charged with 7.0 ml of anhydrous toluene which had previously been degassed and stored under argon and Grubbs II catalyst (22.3 mg, 10 mmol %). The reaction vessel was then degassed three times and heated in an oil bath to 80° C. Purified acryloyl ester 26 (90 mg, 0.35 mmol) was dissolved in 0.5 ml of toluene and added via syringe. The temperature of the oil bath was increased to initiate reflux and the reaction was stirred for 48 h. Then the resulting black solution was concentrated and subjected to flash chromatography (50% ethyl acetate/hexanes) to afford 27 (64 mg, 81%). $R_f$=0.48 (1:1 acetone/hexanes); $[\alpha]_D^{23}$ −97° (c 0.88, CHCl$_3$); $^1$H NMR (CDCl$_3$) δ 6.86 (dd, 1H, J=9.9, 4.7 Hz, H-4), 6.16 (ddd, 1H, J=10.4, 4.0, 2.0 Hz, H-8), 6.16 (dd, 1H, J=9.9, 1.0 Hz, H-3), 6.04 (ddd, 1H, J=10.4, 2.4, 1.0 Hz, H-7), 4.78 (t, 1H, J=4.0, 1.0 Hz, H-8a), 4.60 (t, 1H, J=4.7, 4.0, 1.0 Hz, H-4a), 4.50 (m, 1H, J=8.2, 2.7, 2.4, 2.0 Hz, H-6), 4.45 (dd, 1H, J=10.9, 8.2 Hz, H-9a), 4.02 (dd, 1H, J=10.9, 2.7 Hz, H-9b); $^{13}$C NMR (CDCl$_3$) δ 170.6, 162.1, 142.0, 130.3, 124.1, 124.0, 71.1, 69.0, 63.1, 61.9, 20.7. HRMS (ESI): calcd for C$_{11}$H$_{12}$O$_5$Na [M+Na]$^+$: 225.0763. Found 225.0760.

(4aR,6S,8aR)-6-(Hydroxymethyl)-6,8a-dihydropyrano[3,2-b]pyran-2(4aH)-one (28)

A solution of 27 (44.0 mg, 0.24 mmol) in THF (2 mL) containing a drop of water was added to a stirring suspension of lipase PS 30 (44.0 mg) and the mixture was stirred for 2 days. TLC (50% acetone/hexane) showed complete consumption of starting material and formation of a more polar component. The crude reaction mixture was filtered to remove solids and the filtrate was concentrated to a residue that was purified by flash chromatography (50% acetone/hexanes) to give 28 (33.0 mg, 92%) as an oil. $R_f$=0.25 (50% acetone/hexanes); $^1$H NMR (CDCl$_3$) δ 6.82 (dd, 1H, J=9.9, 3.7 Hz, H-4), 6.07 (d, 1H, J=10.0, 1.6 Hz, H-8), 6.01 (m, 1H, J=10.3, 3.3 Hz, H-8), 5.93 (m, 1H, J=10.3, 2.4, 1.1 Hz, H-7), 4.80 (ct, 1H, J=5.2, 2.5 Hz, H-8a), 4.68 (t, 1H, J=5.2, 3.5, 1.6 Hz, H-4a), 4.28 (m, 1H, J=5.5, 2.0 Hz, H-6), 3.66 (m, 2H, J=6.4, 5.5 Hz, H-9a,9b), 1.85 (bs, 1H, OH); $^{13}$C NMR (CDCl$_3$) δ 162.0, 143.0, 130.5, 124.2, 123.8, 72.9, 69.6, 63.6, 63.1. HRMS (ESI): calcd for C$_9$H$_{10}$O$_4$Na [M+Na]$^+$: 205.0477. Found 225.0480.

(2S,4aR,8aR)-6-Oxo-2,4a,6,8a-tetrahydropyrano[3,2-b]pyran-2-carboxamide (29)

Compound 29 was prepared by adapting the procedure of Kiss and Hell (Kiss, A., and Z. Hell, Tetrahedron Lett., 52: 6021-6023, (2011)) with a change of solvent from methanol to tert-butanol. A mixture of nitrile 4 (0.040 g, 0.226 mmol), Cu$^{II}$-4 Å catalyst (0.022 g), acetaldoxime (0.040 g, 0.678 mmol), and tert-butanol 2 mL) was stirred at 70° C. for 4 h. The mixture was filtered through a pad of Celite® and concentrated to a yellow-brown solid that was purified by cartridge chromatography on a Waters vacuum manifold system using 5% methanol/chloroform as eluant (flash chromatography was also successful using 10% methanol/chloroform). Concentration of fractions left a white solid; yield, 0.0227 g (51.5%). $R_f$ 0.2 (10% methanol/chloroform); mp 160-164° C.; $[\alpha]_D$ −268 (c, 0.8, methanol; IR (ATR) V$_{max}$ 3425, 3325, 3219, 1710, 1670, 1618 cm$^{-1}$; $^1$H NMR (300 MHz, CDCl$_3$) δ 7.10 (dd, 1H, J$_{3,4}$=10.1, J$_{4,4a}$=5.4 Hz, H-4), 6.40 (ddd, 1H, J$_{7,8}$=10.2, J$_{6,7}$=3.6, J$_{7,8a}$=1.2 Hz, H-7), 6.16 (d, 1H, J$_{3,4}$=10.5, H-3), 6.10 (m, 1H, H-8), 4.86 (bs, 2H, NH$_2$), 4.80 (m, 2H, H-6, H-8a), 4.61 (ddd, 1H, J$_{4a,4}$=J$_{4a,8a}$=4.5, J$_{4a,8}$=1.2 Hz, H-4a); $^{13}$C{$^1$H} NMR (CDCl$_3$) δ174.1, 164.8, 143.7, 131.8, 124.5, 123.3, 74.0, 70.2, 64.4. HRMS (ESI-TIF) m/z calcd for C$_9$H$_{10}$NO$_4$ 196.0610. Found 196.0607.

((2R,3R)-3-Acetoxy-6-((trimethylsilyl)ethynyl)-3,6-dihydro-2H-pyran-2-yl)methyl acetate (30)

Using the procedure of Yamada (Chem. Commun., 49: 11221-11223, (2013)), a solution of commercially available 3,4,6-tri-O-acetyl-D-galactal (0.3030 g, 1.1130 mmol) and bis(trimethylsilyl)acetylene (0.3793 g, 2.2260 mmol, 2.0 eq) in anhydrous dichloromethane (10 mL) was stirred in a 3-neck round-bottomed flask that was fitted with a stopper, a 2-way adaptor, and a septum. The reaction solution was cooled to −20° C. (CO$_2$ (s)/i-PrOH), degassed, and placed under argon, after which SnCl$_4$ (2.23 ml, 2.23 mmol, 1M solution in CH$_2$Cl$_2$, 2 eq) was added dropwise via a syringe over 20 minutes. After the addition of SnCl$_4$ the reaction mixture darkened and was allowed to warm to 0° C. The reaction was monitored by TLC (30% ethyl acetate/hexanes) until the starting material was consumed, usually in 1 h, after which the reaction solution was poured a mixture of ice and saturated Rochelle's salt and allowed to stir vigorously for a period of 45 min-1 h. The biphasic solution was extracted with dichloromethane (2×25 mL), washed with saturated NaHCO$_3$ (25 mL) and brine (25 mL), dried (Na$_2$SO$_4$), and concentrated to yield a yellow oil that was purified by flash chromatography to afford 0.2289 g of 30 as a clear, colorless oil. $R_f$=0.45 (30% ethyl acetate/hexanes; $[\alpha]_D^{20}$ −283° (c 1.0, CHCl$_3$); $^1$H NMR: (CDCl$_3$) δ 6.11-5.92 (m, 1H), 5.11-4.96 (m, 1H), 4.39-4.22 (m, 1H), 4.22-4.08 (m, 1H), 2.17-1.95 (m, 3H), 0.26-0.02 (m, 4H); $^{13}$C NMR: (CDCl$_3$) δ 170.73, 170.43, 131.92, 122.39, 100.16, 92.11, 69.68, 64.39, 63.39, 62.94, 20.86, 20.80, −0.26.

(2R,3R)-6-Ethynyl-2-(hydroxymethyl)-3,6-dihydro-2H-pyran-3-ol (31)

A solution of 30 (0.2344 g, 0.7551 mmol) in anhydrous methanol (10 mL) was stirred in a round-bottomed flask as anhydrous K$_2$CO$_3$ (0.4175 g, 3.0204 mmol, 4 eq) was added. Upon addition the solution darkened to a yellow color and the resulting heterogenous mixture was stirred at room temperature. The reaction was monitored by TLC (2:1 ethyl acetate/hexanes), with consumption of starting material typically occurring in 1.5-2 h after which the solution was acidified to a pH of 7 using Dowex® 50×8 resin as indicated by pH paper (1-12). The heterogenous mixture was filtered and the filtrate was concentrated in vacuo to yield an orange solid that was purified by flash chromatography (3:1 ethyl acetate/hexanes) to yield 0.1024 g (88%) of 31 as a white waxy solid that was azeotroped with pentane (5×10 mL) and dried under vacuum overnight. mp 103-105° C.; $[\alpha]_D^{20}$ −541° (c 0.25, CHCl$_3$); $^1$H NMR: (CDCl$_3$) δ 6.01 (ddd, J=9.9, 5.4, 1.9 Hz, 1H), 5.89 (dd, J=10.0, 3.8 Hz, 1H), 4.95 (dt, J=4.0, 2.1 Hz, 1H), 4.01 (ddd, J=6.6, 4.7, 2.2 Hz, 1H), 3.88 (s, 4H), 3.82 (s, 1H), 2.45 (d, J=2.3 Hz, 1H), 2.11 (s, 1H), 1.90 (d, J=9.2 Hz, 1H); $^{13}$C NMR: (CDCl$_3$) δ 128.76, 125.93, 76.42, 76.00, 75.58, 73.81, 72.44, 62.86, 61.81, 61.75, 0.0.

tert-Butyl(((2R,3R)-3-((tert-butyldimethylsilyl)oxy)-6-ethynyl-3,6-dihydro-2H-pyran-2-yl)methoxy)dimethylsilane (32)

A solution of diol 31 (0.5000 g, 3.2432 mmol) in anhydrous DMF (20 mL) was stirred at room temperature as imidazole (1.100 g, 16.2160 mmol, 5.0 eq) was added, followed by the addition of tert-butyldimethylsilyl chloride (1.2700 g, 8.4323 mmol, 2.6 eq). The resulting cloudy yellow solution was allowed to stir at room temperature. Reaction progress was monitored by TLC (10% ethyl acetate/hexanes), with starting material typically consumed after 20-25 h, after which the reaction solution was quenched with saturated NH$_4$Cl and extracted with ethyl acetate (4×10 mL). The combined extracts were washed with water (2×10 mL) and brine (10 mL), dried (Na$_2$SO$_4$), and concentrated in vacuo to yield a yellow oil which was purified by flash chromatography (10% ethyl acetate/hexanes) to yield 0.4500 g (36%) of 32 as a pale yellow oil. $[\alpha]_D^{20}$ −196° (c 1.0, CHCl$_3$); $^1$H NMR: (CDCl$_3$) δ 5.98-5.81 (m, 1H), 5.01-4.93 (m, 1H), 4.04-3.89 (m, 1H), 3.89-3.67 (m, 1H), 3.73 (s, 1H), 2.51-2.39 (m, 1H), 1.05-0.76 (m, 13H), 0.08 (d, J=2.5 Hz, 6H), 0.07 (s, 1H); 13C NMR: (CDCl3) δ 129.36, 127.95, 81.02, 78.01, 77.59, 77.16, 75.45, 74.50, 74.47, 64.03, 63.96, 62.95, 62.78, 62.71, 26.51, 26.45, 18.90, 18.80, −3.51, −4.11, −4.57, −4.70.

((2R,3R)-3-((tert-Butyldimethylsilyl)oxy)-6-ethynyl-3,6-dihydro-2H-pyran-2-yl)methanol (33)

A solution of di-OTBS ether 32 (0.43 g, 1.236 mmol) in anhydrous methanol (20 mL) was stirred in a round bottom flask as pyridinium p-toluenesulfonate (0.0565 g, 0.2247 mmol, 20.0 mol %) was added. The resulting solution was stirred at room temperature. Reaction progress was monitored by TLC (30% ethyl acetate/hexanes), with the majority of starting material typically being consumed after 20-24 h, with only minimal diol formation as shown by TLC, after which the solvent was removed under high vacuum attached to a rotary evaporator whose water bath was maintained at 0° C. The resulting colorless oil was immediately diluted with cold dichloromethane (40 mL), and washed with 0° C. water (15 mL), 0° C. saturated NaHCO$_3$ (10 mL), then dried (Na$_2$SO$_4$) and concentrated to yield 0.2215 g (73%) of 33 as a clear oil that was immediately used without further purification, with an aliquot being removed for optical rotation data and HRMS analysis. $[\alpha]_D^{20}$ −244° (c 1.0, CHCl$_3$). No $^1$H/$^{13}$C NMR was obtained as this compound will readily undergo a migration of the secondary TBS ether to afford the more stable secondary alcohol.

(2S,3R)-3-((tert-Butyldimethylsilyl)oxy)-6-ethynyl-3,6-dihydro-2H-pyran-2-carbaldehyde (34)

a solution of primary alcohol 33 (0.1315 g, 0.4899 mmol) in anhydrous dichloromethane (20 mL) was stirred at 0° C. as DIPEA (0.3799 g, 0.51 mL, 2.9393 mmol, 6 eq), DMSO (0.4592 g, 0.42 mL, 5.8786 mmol, 12 eq), and SO$_3$-pyridine (0.3899 g, 2.4494 mmol, 5 eq) were added. The resulting clear, slightly brown, solution was stirred at 0° C. with reaction progress being monitored by TLC (30% ethyl acetate/hexanes) with consumption of starting material typically occurring in 2-3 h. After the reaction was complete as shown by TLC, the reaction solution was quenched with cold water (30 mL) and extracted with cold ethyl acetate (3×20 mL), the combined extracts were washed with cold water (4×15 mL) and cold brine (10 mL), dried (Na$_2$SO$_4$), and concentrated in vacuo to yield 0.0806 g (62%) of 34 as a red-brown oil. $[\alpha]_D^{20}$ −241° (c 1.0, CHCl$_3$), 1H NMR: (CDCl3) δ 9.63 (d, J=0.6 Hz, 1H), 5.95-5.88 (m, 2H), 5.12 (t, J=2.0 Hz, 1H), 4.36 (td, J=3.1, 1.7 Hz, 2H), 2.51 (d, J=2.3 Hz, 1H), 0.88 (qd, J=2.9, 2.4, 1.6 Hz, 2H), 0.83 (s, 9H), 0.89-0.73 (m, 1H), 0.11-0.02 (m, 1H), 0.06 (s, 4H); 13C NMR: (CDCl3) δ 200.82, 128.88, 126.21, 79.20, 78.44, 77.46, 77.03, 76.61, 75.24, 75.20, 63.22, 63.13, 25.65, 18.02, −4.12, −4.90.

Ethyl (Z)-3-((2R,3R,6S)-3-((tert-butyldimethylsilyl)oxy)-6-ethynyl-3,6-dihydro-2H-pyran-2-yl)acrylate (35)

To a clear, slightly yellow solution of aldehyde 35 (0.0606 g, 0.2275 mmol) in anhydrous methanol (5 mL) was added (carbethoxymethylene)-triphenylphosphorane (0.1189 g, 0.3412 mmol, 1.5 eq). The resulting homogenous solution was stored at −10° C. overnight with reaction progress being monitored by TLC (10% ethyl acetate/hexanes) with starting material typically being consumed in 30-35 h, after which the solvent was removed and the crude product was immediately purified by flash chromatography (10% ethyl acetate/hexanes) to yield 0.0422 g (55%) of 35 a clear oil. $^1$H NMR: (CDCl$_3$) δ6.29 (ddt, J=11.7, 7.0, 1.8 Hz, 1H), 5.99-5.84 (m, 3H), 5.49 (ddd, J=7.0, 2.7, 1.5 Hz, 1H), 5.05-4.97 (m, 1H), 4.29 (td, J=2.8, 1.3 Hz, 1H), 4.28-4.10 (m, 2H), 2.48 (td, J=2.3, 1.2 Hz, 1H), 1.67-1.55 (m, 1H), 1.30 (tt, J=7.1, 1.8 Hz, 3H), 1.04-0.76 (m, 11H), 0.09 (s, 1H).

(4aR,6S,8aR)-6-Ethynyl-6,8a-dihydropyrano[3,2-b]pyran-2(4aH)-one (36)

A solution of ester 35 (0.0370 g, 0.1100 mmol) in anhydrous methanol (2 mL) was heated to reflux after which p-toluene sulfonic acid (0.0032 g, 0.0165 mmol, 15.0 mol %) was added. The resulting colorless solution was stirred in a round-bottomed flask with reaction progress being monitored by TLC (30% ethyl acetate/hexanes). Starting material was typically consumed after 5-6 h, after which the methanol was removed by a rotary evaporator, and toluene was added to the reaction vessel. The resulting clear, colorless, solution was allowed to stir overnight at reflux with starting material typically being consumed after an additional 20 h (~26 h in total). The reaction solution was concentrated in vacuo to yield a brown, crystalline solid that was purified by flash chromatography (30% ethyl acetate/hexanes) to yield 0.0104 g (53%) of 36 as a white crystalline solid. mp 153-154° C.; $[\alpha]_D^{20}$ 338° (c 1.0, CHCl$_3$); $^1$H NMR: (CDCl$_3$) δ 6.94-6.83 (m, 3H), 6.31-6.19 (m, 3H), 6.22-6.02 (m, 7H), 5.09-4.97 (m, 3H), 4.64 (dd, J=5.0, 3.1 Hz, 3H), 4.58-4.48 (m, 3H), 3.52-3.42 (m, 1H), 2.80-2.69 (m, OH), 2.64-2.53 (m, 3H), 1.26 (s, 2H), 1.25 (d, J=1.3 Hz, 1H), 0.06 (d, J=0.5 Hz, 1H); $^{13}$C NMR: (CDCl$_3$) δ 162.34, 140.08, 131.89, 125.03, 121.68, 78.77, 77.44, 77.02, 76.59, 75.74, 68.59, 63.55, 61.12.

(4aR,6S,8aR)-6-(2H-Tetrazol-5-yl)-6,8a-dihydropyrano[3,2-b]pyran-2(4aH)-one (37)

A solution of pyranopyran 4 (0.0354 g, 0.2000 mmol) in anhydrous toluene (2 mL) was stirred at 80° C. as TMSN$_3$ (53.1 µL, 0.4000 mmol, 2 eq) was added via a micropipette, followed by the addition of Bu$_2$SnO (0.0049 g, 0.02 mmol, 10.0 mol %). The resulting solution was stirred at 80° C. and was allowed to proceed overnight with reaction progress being monitored by TLC (ethyl acetate). Overnight the reaction solution darkened in color, with starting material showing trace presence after 45 h, therefore a minimum of silica gel was added to the reaction vessel, and the reaction solution was concentrated in vacuo to coat the silica gel, which was immediately placed onto a silica gel column packed with the eluting solvent (10:89:1 methanol/dichloromethane/triethyl amine) to afford 0.0421 g (95%) of a dark brown oil. HRMS (ESI): m/z calcd for C$_9$H$_7$N4O$_3$ [M−H]$^+$: 219.0518. Found 219.0521.

Results and Discussion: In our first approach to pyranopyran (2), we chose a Type 1 strategy in which a nitrile group was introduced by a Ferrier rearrangement to the anomeric center of D-galactal (Scheme 1):

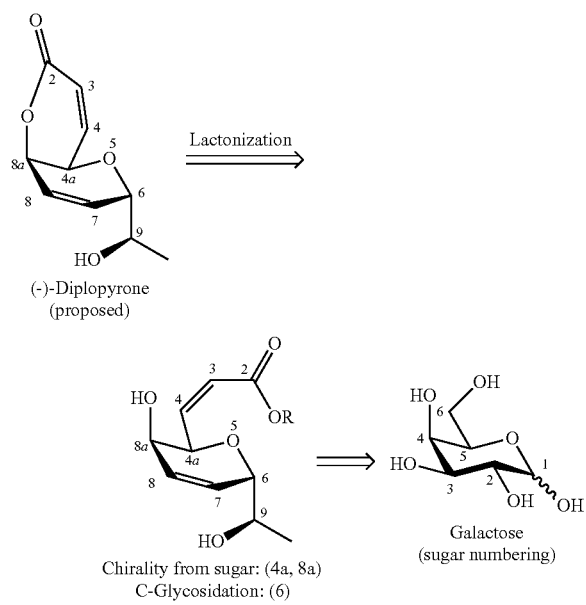

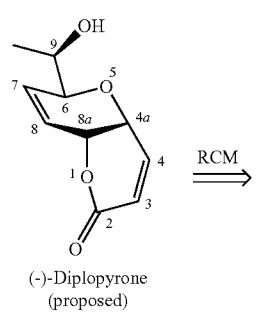

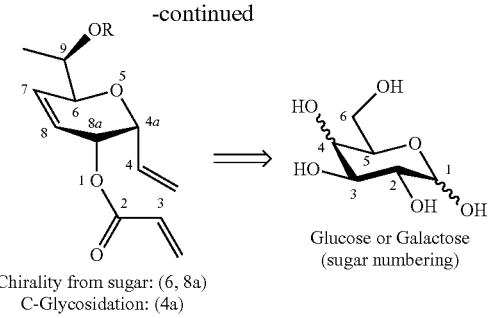

Chirality from sugar: (6, 8a)
C-Glycosidation: (4a)

Figure 1:
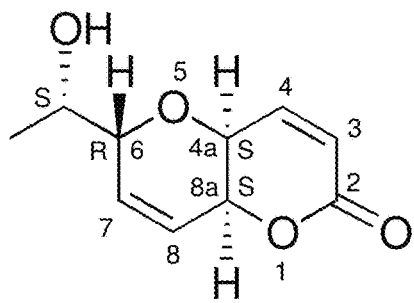
FIG. 1 shows putative (+)-diplopyrone (1) and related compounds in this Study as described below.
Figure 1:
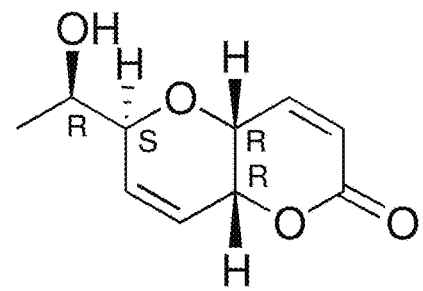
Figure 1:
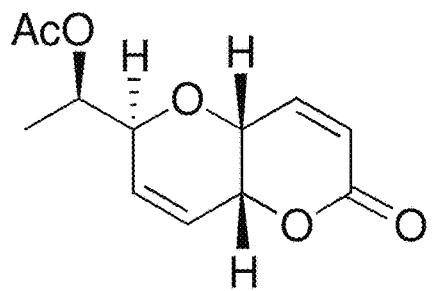
Figure 1:
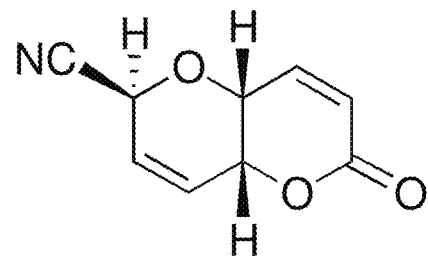
Figure 2:
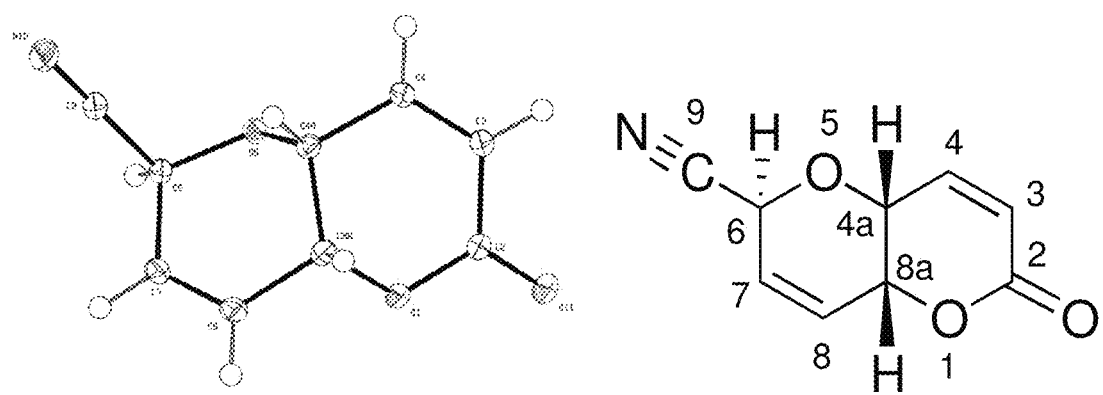
FIG. 2 shows (Oak Ridge Thermal Elipsoid Plot) ORTEP diagram of nitrile pyranopyran (4) as described below.

The nitrile group was then converted to the required hydroxyethyl side-chain prior to chain extension and lactonization. Tri-O-acetyl-D-galactal (5) was treated with trimethyl-silyl cyanide in the presence of boron trifluoride diethyl etherate to provide crystalline glycosyl nitrile (6) in 60% yield on a 20-gram scale (Rotella, M. R., et al., Carbohydr. Res., 425: 40-42 (2106)). Deacylation of glycosyl nitrile (6) with p-toluenesulfonic acid in methanol gave diol nitrile (7) which was converted to di-O-TBS ether (8) in 91% overall yield. The nitrile (8) was a suitable precursor for the hydroxyethyl side-chain by either of two sequences, without being bound by theory, one involving reduction to the corresponding aldehyde followed by methylation and the other involving prior methylation of 8 to give a methyl ketone which could be reduced. Our attempts at conversion of the nitrile to the hydroxyethyl side chain of pyranopyran (2) by both of these sequences were surprisingly unsuccessful. Ether (8) and similar compounds were found to be prone to double bond migration, epimerization at the anomeric center in the presence of base, and vinylogous β-elimination. For example, addition of methyllithium to ether (8) followed by hydride reduction of the resulting ketone gave a hydroxyethyl derivative in 14% overall yield, along with products of elimination. In spite of these difficulties, it was surprisingly possible to construct the pyranopyran core of diplopyrone from ether (8), leaving the nitrile group intact, which provided access to an interesting compound (4) for biological studies (vide infra). Selective deprotection of the 6-hydroxyl group of ether (8) was achieved using PPTS in methanol at room temperature. Migration of the 4-O-TBS group in alcohol (9) to the C-6 hydroxyl group was observed to occur upon standing at room temperature so it was necessary to carry out the next two steps in quick succession. Oxidation of the primary alcohol (9) by the Parikh-Doering method gave aldehyde (10) in 86% yield. Surprisingly, attempted Wittig reactions of aldehyde (10) with methylene triphenylphosphorane failed as did Peterson alkenation, again, without being bound by theory, likely the result of the tendency for aldehyde (10) to undergo vinylogous 3-elimination of the 4-O-TBS group; Tebbe methylenation was also unsuccessful. The reaction of aldehyde (10) with stabilized Wittig reagent (carbethoxymethylidene)triphenylphosphorane under conditions described by Valverde et al. (Tetrahedron, 43: 1895-1901 (1987)) gave ester (11) exclusively as the Z isomer. The cyclization of ester (11) to diplopyrone nitrile (4) surprisingly proved more difficult than expected, perhaps, without being bound by theory, because the double bond in the pyranose ring places the C-4 hydroxyl and ester groups in poor proximity for ring closure. However, we were surprisingly able to obtain nitrile (4) in 88% overall yield from ester (11) by a two-step procedure involving deprotection in methanol then heating in toluene, both in the presence of an acid catalyst (specify; e.g., p-toluenesulfonic acid. The overall yield of nitrile (4) from galactal derivative (5) was 20%. Nitrile (4) was crystalline and suitable for analysis by X-ray diffraction. The ORTEP diagram of nitrile (4) is depicted in FIG. 2. The general synthesis scheme for pyranopyran nitrile (4) is as follows:

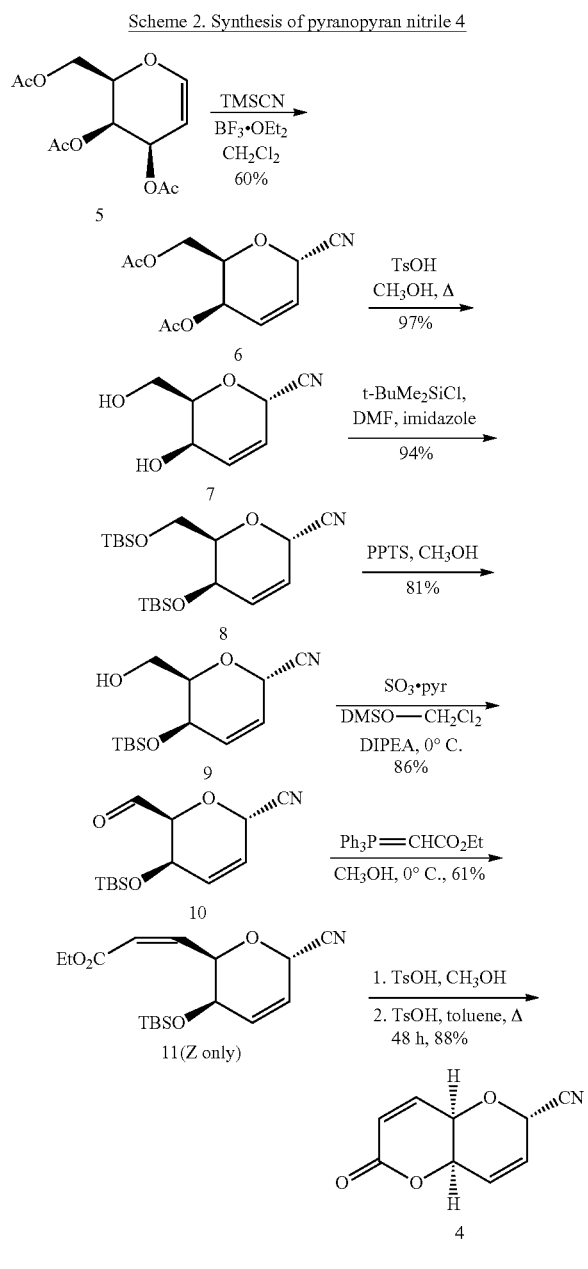

The pyranopyran nitrile 4 turned out to be an interesting compound, especially in view of its biological activity discussed later. However, our surprisingly lack of success in converting the nitrile group to a hydroxyethyl side-chain prompted us to explore an alternative (Type 2, Scheme 1) strategy for the synthesis of pyranopyran (2). In this approach, the hydroxyethyl group was introduced first, by chain extension at C-6 of a hexopyranoside. While many methods exist for the synthesis of higher-carbon sugars (Györgydeák, Z., and I. F. Pelyvás, 1989), a surprising challenge that emerged in the route to our target compounds was the control of stereochemistry at the off-ring, C-9 chirality center. Additions of organometallic reagents to dialdopyranosides (I) typically favor products (II) that result from chelation-control and which possess the incorrect stereochemistry for diplopyrone (FIG. 3)(Kasatkin, A. N., et al., Chem. Bull., 42: 1078-1082 (1993)). Felkin-Anh stereoselectivity (III) was required for our synthesis. A second surprising challenge in this approach was the need for an efficient synthesis of a C-vinyl glycoside precursor for the RCM (ring-closing metathesis)-based route to the lactone (Scheme 1). C-Vinyl glycosides have been used as precursors to carbon-linked glycoconjugates, for example, C-galactosyl ceramides (Chen, 2004). However, unlike their C-allyl glycoside counterparts (Aliti, A. S., and D. R. Mootoo, Org. Lett., 16: 1466-1469 (2014); Giannis, A., and K. Sandhoff, Tetrahedron Lett., 26: 1479-1482 (1985); Cipolla, L., et al., Tetrahedron: Asymm., 11: 295-303 (2000)), simple, unsubstituted C-vinyl glycosides surprisingly proved to be more difficult to synthesize as illustrated in recent approaches to C-alkyl, C-aryl, and (substituted) C-vinyl glycosides, some of which are based on modern catalytic methods (Nolen and Feeney, 2014; Nicolas et al., 2012; Gong et al., 2007). We were surprisingly able to solve both the chain-extension and C-vinyl glycoside problems in our approach.

Commercially available 1,2:3,4-di-O-isopropylidene-α-D-galactopyranose (12) was oxidized with catalytic TEMPO in the presence of bis(acetoxy)iodo-benzene (BAIB) on a 15-gram scale to give aldehyde (13) which was used immediately in the next step (Scheme 3)(De Mico, A., et al., J. Org. Chem., 62: 6974-6977):

Scheme 3. Chain extension and C-glycosidation for pyranopyran synthesis

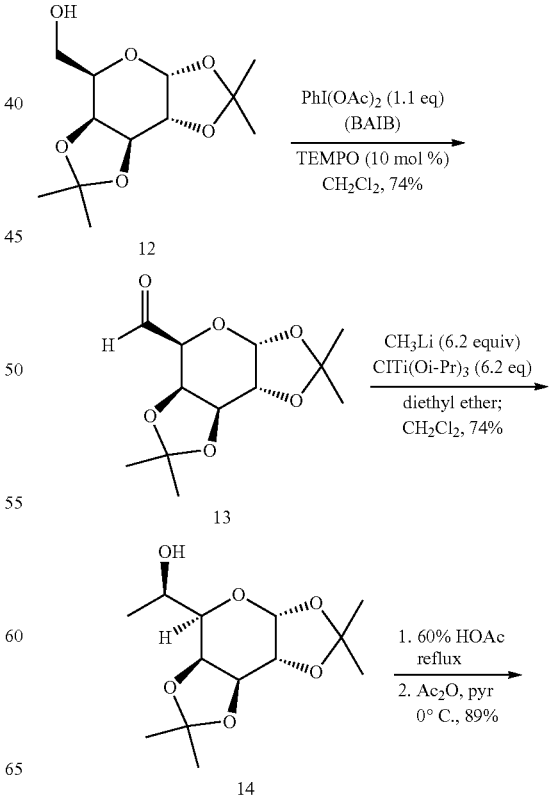

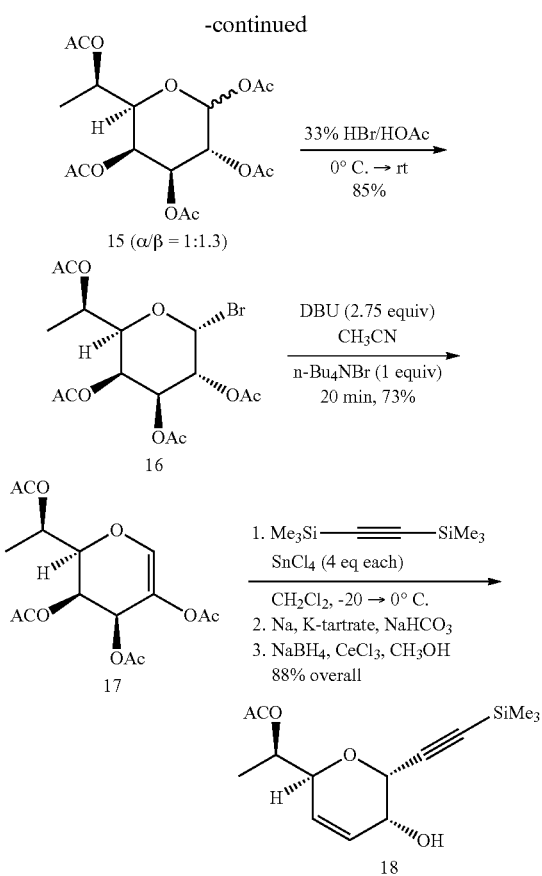

This oxidation was also carried out using a polymer-bound bromite complex (Brunjes, M., et al., Adv. Synth. Catal., 345: 635-642 (2003)), which gave improved yields on smaller (1-2 mmol) scales, but turned out to be surprisingly less desirable for scaled-up preparations of aldehyde (13). The addition of organometallic reagents to aldehyde (13) has provided products that have found use as building blocks for trisaccharides used to study monoclonal antibodies (Lemieux, R. U., et al., Can. J. Chem., 60: 81-86 (1982)), enzyme inhibitors (Sabesan, S., et al., Carbohydr. Res., 267: 239-261 (1995)), and higher-carbon sugars (Györgydeák and Pelyvás, 1989). However, most of the addition reactions of organometallic reagents to aldehyde (13) provide mixtures of diastereomers with the highest selectivity for compound (14) on the order of 2.5:1 to 3.0:1 (Kasatkin et al., 1993). Our previous studies (Giuliano, R. M., and F. J. Villani, Jr., J. Org. Chem., 60: 202-211 (1995)) of the addition of organometallic reagents to pentodialdo-1,4-furanoses revealed high levels of Felkin-Anh stereoselectivity when methyl(triisopropoxy)titanium (Rausch, M. D., and H. B. Gordon, J. Organomet. Chem., 74: 85-90 (1974); Weidmann, B., and D. Seebach, Helv. Chim. Acta, 63: 2451-2454 (1980)) was used instead of methyllithium or Grignard reagents. In need of a highly stereoselective route to compound (14), we decided to examine the addition of methyl(triisopropoxy)titanium to aldehyde (13) and were able to achieve a d.r. of 19:1 in favor of the desired compound (14) on a 4-gram scale (Vagadia, P. P., et al., Carbohydr. Chem: Proven Synthetic Methods, 3: 245-253 (2015)). In the larger-scale preparation included herein, the minor isomer was estimated at 0.7%. The structure of compound (14) was assigned based on comparison of NMR data with that published by Lemieux (1982). Further confirmation of the structure of compound (14) was provided by x-ray analysis of the corresponding p-bromobenzoate, which surprisingly showed that the configuration at the newly formed C-9 chirality center is R (Wagadia et al., 2015). The yield and stereoselectivity of the methyltitanium-based route to chain-extension were surprisingly critical to the overall success of our synthesis. Surprisingly, two of the four chirality centers of pyranopyran (2), C-6 and C-9, were established in compound (14) without the production of diastereomers.

The second challenge in a Type II route to pyranopyran (2) was surprisingly the synthesis for the C-vinyl glycoside needed for the lactone by RCM. Progress in the development of methods for the synthesis of C-alkynyl glycosides (Chang, W.-C., and M. Isobe, Tetrahedron, 70: 8324-8333 (2014); Isobe, M., et al., Chem. Commun., pages 2665-2676 (1998); Tatina, M. B., et al., Org. Biomol. Chem., 12: 7900-7903 (2014)) suggested that a sequence consisting of C-alkynylation followed by Lindlar reduction would provide the vinyl glycoside needed as the RCM precursor. This approach was investigated by Franck and coworkers in their synthesis of C-galatosyl ceramides (Chen, G., et al., Org. Lett., 6: 4077-4080 (2004)); however, unexpectedly low overall yields of C-vinyl glycoside from methyl galactopyranoside led the authors to pursue an alternative synthesis. As shown in Scheme 3, glycal (17) was prepared from compound (14) by a four-step sequence involving deisopropylidenation, acylation, and bromination which gave glycosyl bromide (16), which was converted to glycal (17) by a modification of the procedure of Ferrier (Grabowski, U., et al., Carbohydr. Res., 305: 351-361 (1998); Ferrier, R. J., IN Methods in Carbohydrate Chemistry VI, Whistler, R. L., and J. BeMiller, Eds., Academic Press, New York, 1972, pp 307-311). Substitution of 1,8-diazabicyclo[5.4.0]undec-7-ene (DBU) for diethylamine in the elimination step surprisingly gave fewer side products. The C-alkynylation of glycal (17) with bis(trimethylsilyl)acetylene, using conditions described by Isobe et al. (1998) for glycals, followed by hydrolytic workup and sodium borohydride reduction as described surprisingly gave exclusively alkynyl alcohol (18) in 88% overall yield. Four transformations surprisingly occurred in this two-step sequence: Ferrier rearrangement, enol acetate hydrolysis, β-elimination of the C-4 acetoxy group, and ketone reduction. Surprisingly the C-3-C-4 double bond in compound (18) was in the correct location of diplopyrone and the configurations at C-1 and C-2 were introduced with complete stereoselectivity. At this point in the synthesis, all four of the chirality centers were surprisingly established.

Final transformations surprisingly culminating in a successful synthesis of the target pyranopyran (2) are shown in Scheme 4:

Scheme 4. Completion of the synthesis of pyranopyran 2

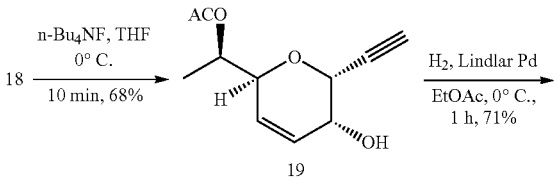

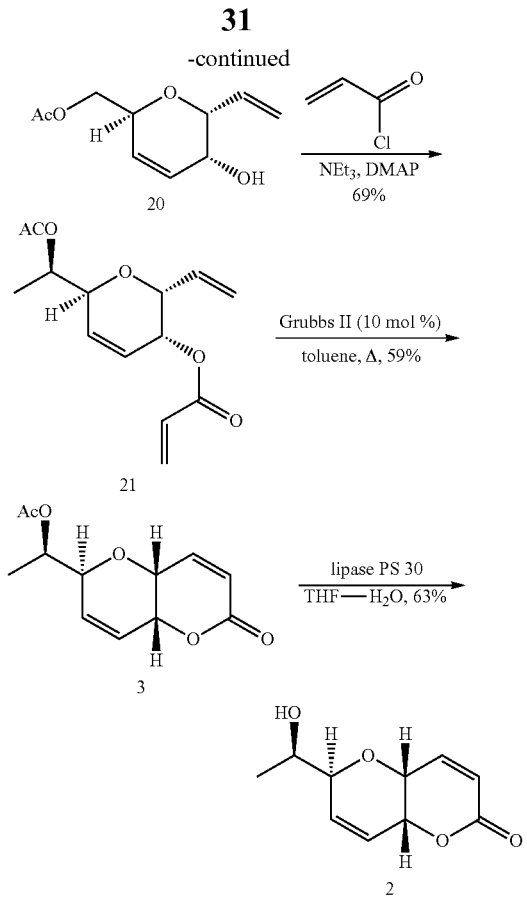

Desilylation of alkyne (18) with TBAF gave alkynyl glycoside (19) in 68% yield. Selective reduction of the alkyne in alkynyl glycoside (19) surprisingly proved challenging with initial attempts with Lindlar's catalyst in methanol producing mixtures of C-vinyl and C-ethyl glycosides. Careful optimization of this reaction in terms of catalyst preparation (pre-treatment with quinoline under hydrogen), solvent (ethyl acetate), and temperature (0° C.) surprisingly led to an efficient reduction of alkynyl glycoside (19) to C-vinyl glycoside (20) with only trace amounts of over-reduced product. Acryloylation of C-vinyl glycoside (20) and RCM using Grubbs II catalyst in toluene surprisingly gave pyranopyran acetate (3). Deacylation of pyranopyran acetate (3) was expected to be challenging due to the presence of the unsaturated lactone which precluded the use of sodium methoxide in methanol which is known to undergo conjugate addition with carbohydrate enones (Thiem, J., and J. Elvers, Chem. Ber., 111: 3514-3515 (1978)). Deacylation with methanol and p-toluenesulfonic surprisingly gave (−)-diplopyrone that was contaminated with a side-product that appeared, without being bound by theory, to be the result of conjugate addition of methanol to the unsaturated lactone. Lipases have been shown to catalyze selective deacylations in carbohydrate esters and we had some previous success in kinetic resolutions in our laboratory (Noecker, L. A., et al., Tetrahedron: Asymm., 9: 203-212 (1998)). Several lipases were assayed against pyranopyran acetate (3) and acceptable results were obtained with Amano PS-30 lipase which gave pyranopyran (2) in 63% yield (80% based on recovered 3).

Figure 3:
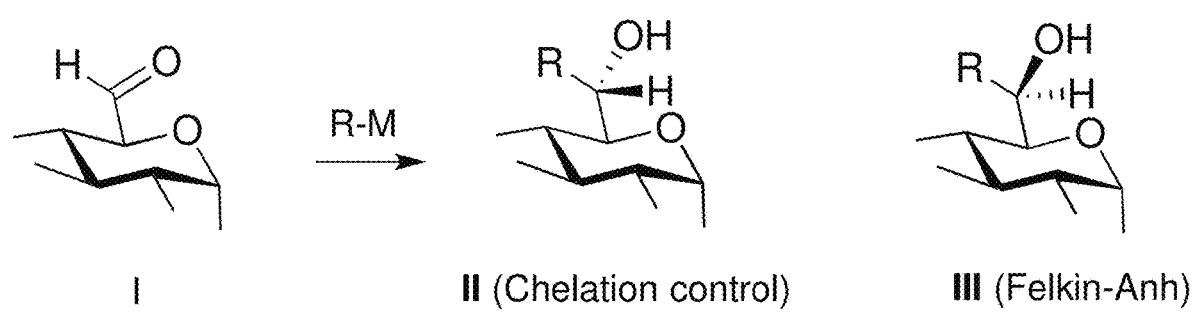
FIG. 3 shows chelation vs. Felkin-Anh stereoselectivity in dialdohexopyranosides as described below.

Enzyme-catalyzed deacylation of pyranopyran acetate (3) was slower than that reported for primary alcohols, but nonetheless was reproducible and surprisingly less complicated by side-product formation than methanolysis. The route from commercially available 1,2:3,4-di-O-isopropylidene-α-D-galactopyranose (12) to pyranopyran 2 requires 13 steps, is highly stereoselective, and proceeds in 4% overall yield. Our route compares favorably with the published route from butanediol (17 steps)(Maity et al., 2017). The final product pyranopyran (2) obtained in our synthesis was crystalline, while natural and synthetic diplopyrone (1) were reported as oils. Pyranopyran acetate 3 was also crystalline and suitable for x-ray analysis. The ORTEP diagram for pyranopyran acetate (3) is shown in FIG. 3 and confirms the structure as being enantiomeric to that reported for natural diplopyrone (1); in other words, the configurations of all of the chirality centers in (3) are opposite to those of (1).

One of the goals of this study was to attempt to clarify the differences in analytical data, in particular NMR data, reported for diplopyrone (1) isolated from the natural source with data obtained for material in the synthesis of putative (+)-diplopyrone" (Maity et al., 2017). As shown herein, the NMR data of pyranopyran (2) synthesized in this study match that reported for putative (+)-diplopyrone by Maity et al. (2017). The same discrepancies were observed when the data for pyranopyran (2) were compared to that reported for the natural product, most notably in proton chemical shifts for H-4a and H-8a, but also in other peak values. The structure was originally assigned on the basis of computational methods and NMR data (Evidente et al., 2003; Giorgio et al., 2005). While the structure is in need of revision, it is difficult to determine exactly where it is incorrect. The 2D 1H NOE (NOESY) data did not show an effect from H-4a to H-6, which would be consistent with a trans relationship of H-6 to both H-4a and H-8a (Evidente et al., 2003).

X-ray diffraction studies of (4): A single colorless block (0.4×0.3×0.2 mm$^3$) grown from ethyl acetate/hexanes was selected and mounted using NVH immersion oil onto a nylon fiber and cooled to the data collection temperature of 100 K with a stream of dry nitrogen gas. Data were collected on a Brüker-AXS Kappa APEX II CCD diffractometer with 0.71073 Å Mo-Kα radiation. Unit cell parameters were obtained from 60 data frames, 0.5° φ from three different sections of the Ewald sphere and complete data collection strategies were determined for each crystal using the APEX2 suite (APEX2. Bruker AXS Inc., Madison, Wis.). The data set consisting of 33419 reflections (4104 unique, $R_{int}$=2.05%) was collected over θ=2.612 to 36.270° and treated with SADABS absorption corrections based on redundant multi-scan data (SADABS-2014/5. Bruker AXS Inc., Madison, Wis.). The systematic absences were consistent with the orthorhombic space group $P2_12_12_1$. The structures was solved by direct methods (XT) and refined by least squares method on $F^2$ using the XL program package interfaced through OLEX2 (Sheldrick, G. M., Acta Cryst., A71: 3-8 (2015); Sheldrick, G. M., Acta Cryst. A64: 112-122 (2008); Dolomanov, O. V., et al., J. Appl. Cryst. 42: 339-341 (2009)). All non-hydrogen atoms were refined with anisotropic displacement parameters and all hydrogen atoms were treated as idealized contributions. The chirality was chosen based on a known stereocenter in the synthesis. The goodness of fit on $F^2$ was 1.108 with $R_1$=2.89% [I>2σ](I)], $wR_2$=8.05% (all data) and with a largest difference peak and hole of 0.436 and −0.167 e/Å$^3$. This structure has been deposited with the CCDC under deposition number 1844126, and is depicted in FIG. 2.

Figure 4:
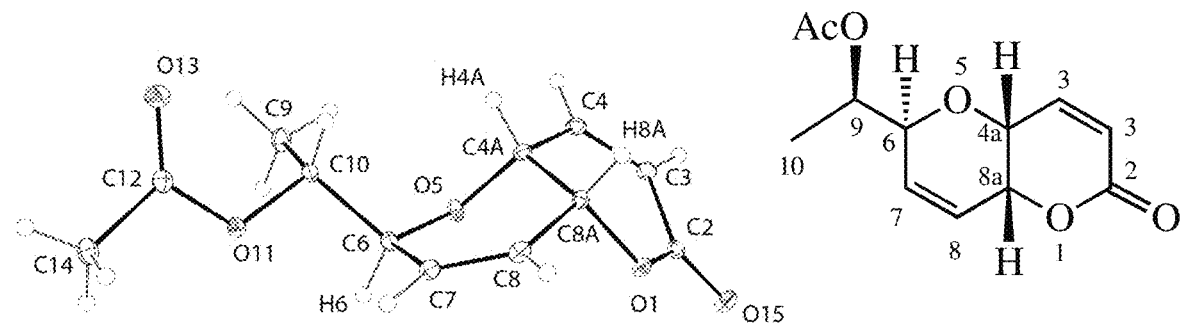
FIG. 4 shows ORTEP diagram of pyranopyran acetate (3).
Figure 5:
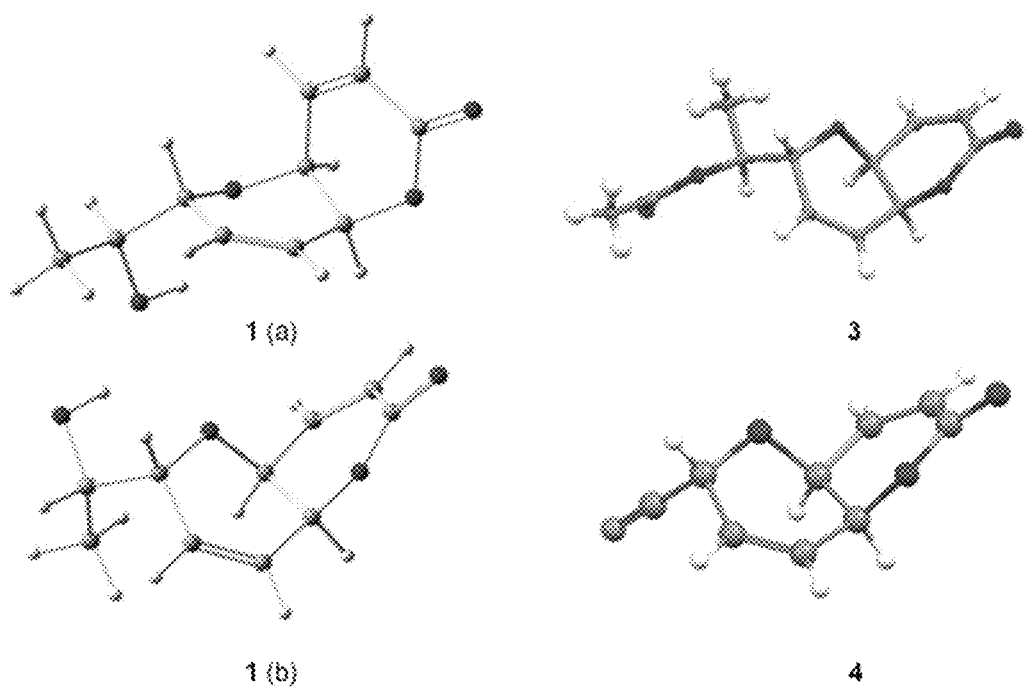
FIG. 5 shows comparison of conformations of pyranopyran acetate (3) and nitrile (4) from crystallographic data with calculated structures reported for diplopyrone (1) as described below.

It is interesting to compare the conformations of compounds 3 and 4 obtained by x-ray analysis with the calculated conformation reported in the literature for (+)-diplopyrone 1 (Giorgio et al., 2005). To facilitate this comparison, ORTEP structures of 3 and 4 can be inverted to show corresponding absolute stereochemistry (FIG. 4). On the basis of molecular mechanics (MMII) calculations performed on the proposed structure of 1, two main conformers were predicted in which the major differences were in the conformation of the hydroxyethyl side chain and the ring to which it is attached. The major conformation predicted from these calculations is indicated as (a) in FIG. 4, while the minor conformation is (b). Our crystallographic analyses of pyranopyran acetate 3 and nitrile 4 indicated solid state conformations for both that more closely match (b).

The starting glycal in our synthesis (Scheme 5) is 22 which is readily available from acetobromoglucose or acetobromogalactose by the reported preparation (Ferrier, R. J., IN: Methods in Carbohydrate Chemistry, VI; R. L. Whistlerand J. N. BeMiller Eds; Academic Press: New York, 307-311 (1972):

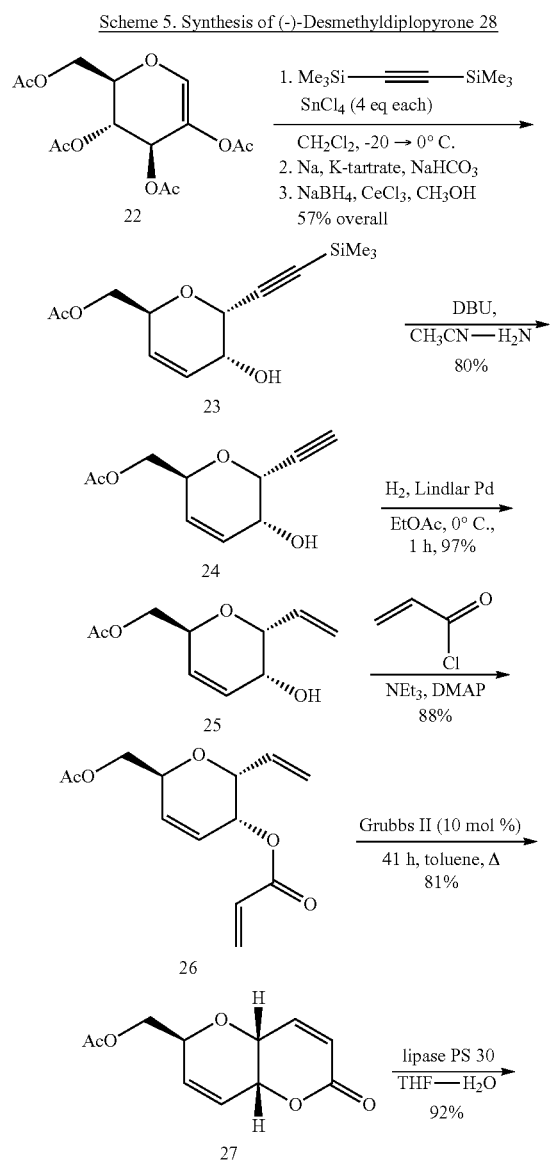

Scheme 5. Synthesis of (-)-Desmethyldiplopyrone 28

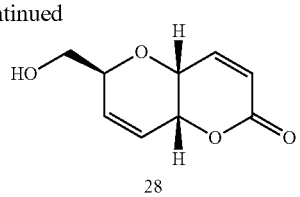

28

The C-alkynylation of 22 with bis(trimethylsilyl)acetylene as described by Chang and Isobe (Chang, W.-C., and M. Isobe, Tetrahedron, 70: 8324-8333 (2014), followed by hydrolytic workup and sodium borohydride reduction as described gave exclusively alkynyl alcohol 23 in 57% overall yield with the desired stereochemistry at C-2 and the C-3-C-4 double bond in the correct location of diplopyrone. Four transformations occur in this two-step sequence: Ferrier rearrangement, enol acetate hydrolysis, 3-elimination of the C-4 acetoxy group, and ketone reduction. Selective deprotection with DBU gave alkyne 24. Selective reduction of the alkyne in 24 to the C-vinyl glycoside proved challenging with initial attempts with Lindlar's catalyst in methanol producing mixtures of C-vinyl 25 and C-ethyl glycosides. Careful optimization of this reaction in terms of catalyst preparation, solvent (ethyl acetate), and temperature (0° C.) surprisingly led to an efficient (97%) reduction of C-alkynyl to C-vinyl glycoside 25 with only trace amount of over-reduced product. The sequence from starting glycal proceeds in 44% overall yield. Acryloylation of 25 set up the key lactone ring closure of 26 by RCM, which occurred with Grubbs II catalyst in toluene at 80° C. to give 27. The reaction time was longer than expected, perhaps because one of the alkenes was electron-deficient. Carbohydrate deacylation is typically carried out with sodium methoxide in methanol; however, sugar enones are known to react rapidly with methoxide and we were concerned that side reactions might occur with 27 under these conditions. We subjected 27 to Amano PS-30 lipase in wet THF and surprisingly observed clean deprotection to give desmethyldiplopyrone 28 in 92% yield.

Pyranopyran amide 29 was prepared in one step from pyranopyran nitrile 4 as shown in Scheme 6:

Scheme 6. Synthesis of Pyranopyran Amide 29

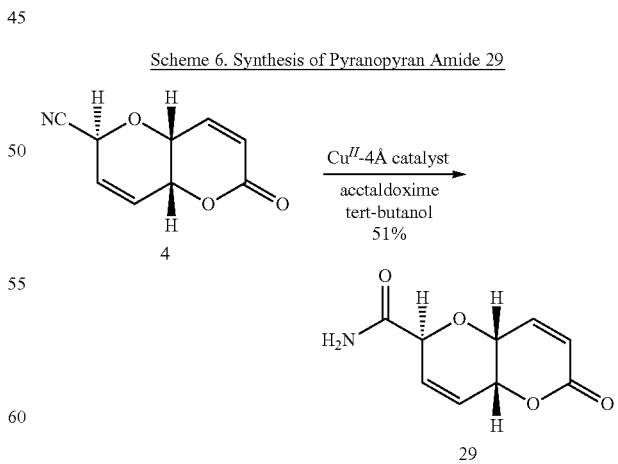

Chemoselective hydration of the nitrile group in the presence of the other functionalities in 4 was carried out by a catalytic method using a copper catalyst on molecular sieves in the presence of acetaldoxime. This method was used previously on nitriles but not those related to 4 (Kiss, A., and Z. Hell, Tetrahedron Lett., 52: 6021-6023, (2011)).

Pyranopyran alkyne 36 was prepared as shown in Scheme 7:

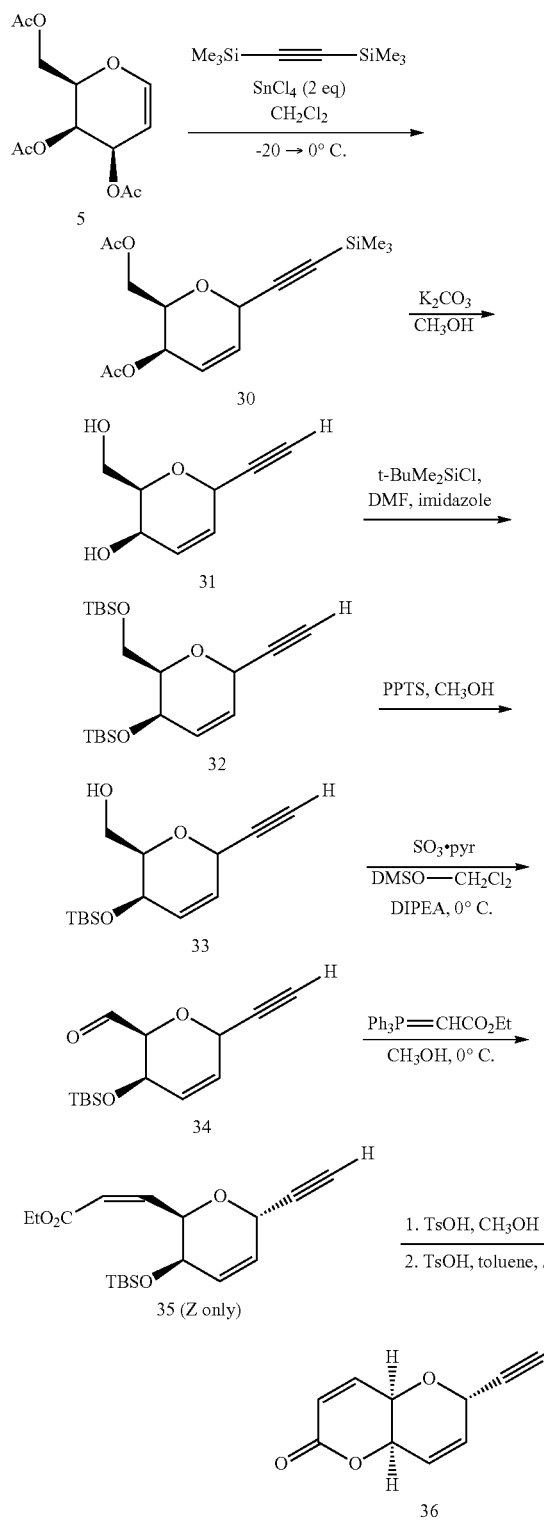

The synthetic route is analogous to that shown in Scheme 2 that was used to synthesis pyranopyran nitrile 4. The addition of azide to pyranopyran nitrile to give a tetrazole using either zinc chloride/sodium azide or ammonium azide was unsuccessful. However, applying conditions described by Somsák for other carbohydrate nitriles compound 37 was obtained (Carbohydr. Res. 346: 1427-1438 (2011)), as shown in Scheme 8:

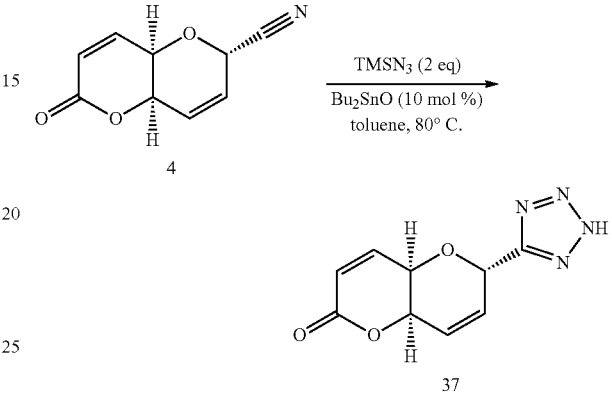

Biological Evaluation: Pyranopyran (2), pyranopyran acetate (3), and pyranopyran nitrile (4) were evaluated for phytotoxic and antibacterial activity. Antibacterial activity was evaluated using common pathogenic bacteria found in catfish. The largest segment of aquaculture in the United States of America is pond-raised catfish, with most production occurring in Mississippi. The most common bacterial diseases in pond-raised catfish are enteric septicemia in catfish (ESC) and columnaris disease which are caused by *Edwardsiella ictaluri* and *Flavobacterium columnare*, respectively. These diseases can cost the catfish industry over US$100 million annually (Schrader, K. K. N., Am. J. Aquacult., 70: 147-153 (2008)). Catfish producers use numerous approaches to manage bacterial diseases in catfish ponds, including the use of medicated feed containing the antibiotic florfenicol, live attenuated vaccines, and chemical therapeutants such as peroxides, copper sulfate ($CuSO_4 \cdot 5H_2O$), and potassium permanganate ($KMnO_4$). However, the use of chemicals in catfish ponds must be carefully monitored because these compounds have broad-spectrum toxicities toward non-target species, such as catfish and planktons. The discovery of efficacious natural or natural-based compounds that are toxic towards *E. ictaluri* and *F. columnare* would provide catfish producers with another beneficial management approach. During our initial screening to discover efficacious antibacterial compounds against *E. ictaluri* and *F. columnare*, we evaluated pyranopyran (2), pyranopyran acetate (3), and pyranopyran nitrile (4) using a rapid bioassay.

An isolate of *F. columnare* [isolate ALM-00-173 (genomovar II)] was obtained from Dr. Covadonga Arias (School of Fisheries, Aquaculture and Aquatic Sciences, Auburn University, Auburn, Ala.). In order to assure purity, cultures of *F. columnare* ALM-00-173 were maintained separately on modified Shieh (MS) agar plates (pH 7.2-7.4) (Decostere, A., et al., Laboratory Animals, 36: 396-402 (2003)). Prior to conducting the bioassay, colonies of *F. columnare* ALM-00-173 were used to prepare the assay culture material by culturing in 75 mL of MS broth for 24 h at 29±1° C. at 150 rpm on a rotary shaker (model C24KC; New Brunswick Scientific, Edison, N.J.). After overnight incubation, a 0.5 McFarland standard of *F. columnare* ALM-00-173 culture material was prepared by transferring cells from the broth culture to fresh MS broth (Schrader, K. K., and M. D. Harries, Aquaculture Research, 37: 928-937 (2006)).

An isolate of *E. ictaluri* (isolate S02-1039) was obtained from Mr. Tim Santucci (formerly with the College of Veterinary Medicine, Mississippi State University, Stoneville, Miss.). In order to assure purity, cultures of *E. ictaluri* S02-1039 were maintained on 3.8% Mueller-Hinton (MH) agar plates (pH 7.3) (Becton, Dickinson and Company, Sparks, Md.). Prior to conducting the bioassay, colonies of *E. ictaluri* S02-1039 were used to prepare assay culture material by aseptically transferring bacterial cells from colonies to 45 mL of 3.8% MH broth to form a bacterial cell density of 0.5 McFarland standard.

The pure test compounds (−)-diplopyrone and (−)-diplopyrone acetate were dissolved in technical grade 100% methanol while (−)-diplopyrone nitrile was dissolved in technical grade 100% acetone. The three test compounds were evaluated for antibacterial activity against *F. columnare* ALM-00-173 and *E. ictaluri* S02-1039 using a rapid 96-well microplate bioassay and following previous procedures (Schrader and Harries 2006). Florfenicol was included as a positive drug control. Control wells (no test material added) were also included in each assay. Final test concentrations of compounds and florfenicol were 0.01, 0.1, 1.0, 10.0, 100.0, and 1000.0 µM. Three replications were used for each dilution of each test compound and drug control, and final results were converted to units of mg/L to allow comparison with previous studies.

The 24-h 50% inhibition concentration ($IC_{50}$) and minimum inhibitory concentration (MIC) were determined using sterile 96-well (flat bottom) polystyrene microplates (Corning Costar Corp., Acton, Mass.) for (−)-diplopyrone and (−)-diplopyrone acetate. In order to prevent solvent interaction with polystyrene, sterile 96-well (flat bottom) quartz microplates (Hellma Cells, Inc., Forest Hills, N.Y.) were used for (−)-diplopyrone nitrile. Initially, dissolved test compounds or florfenicol were micropippeted separately into individual microplate wells (10 µL/well), and the solvent was allowed to completely evaporate before 0.5 McFarland bacterial culture was added to the microplate wells (200 µL/well). Microplates were incubated at 29±1° C. (VWR model 2005 incubator; Sheldon Manufacturing, Inc., Cornelius, Oreg.). A microplate photometer (SpectraCount, Packard Instrument Company, Meriden, Conn.) was used to measure the absorbance (630 nm) of the microplate wells at time 0 and 24-h. Two replicates of each microplate bioassay were made. Cell viability of *F. columnare* ALM-00-173 and *E. ictaluri* S02-1039 was determined at the completion of the growth bioassay for each test compound using the yellow dye 3(4,5-dimethylthiazol-2-yl)-2,5-diphenyl tetrazolium bromide (MTT) and previously outlined procedures (Schrader and Harries 2006). In addition, the minimum bactericidal concentration (MBC) was determined for very active compounds (Schrader and Harries 2006).

The means and standard errors of absorbance measurements were calculated, graphed, and compared to controls to determine the MIC, 24-h $IC_{50}$, and MTT 24-h $IC_{50}$ for each test compound. The 24-h $IC_{50}$ and MIC results for each test compound were divided by the respective 24-h $IC_{50}$ and MIC results obtained for the positive control florfenicol to determine the relative-to-drug-control florfenicol (RDCF) values.

Pyranopyran nitrile (4) was surprisingly the most active of the three test compounds against *F. columnare* ALM-00-173, with a MIC of 17.7±0 mg/L, 24-h $IC_{50}$ of 7.5±0.5 mg/L, and 24-h cellular viability $IC_{50}$ of 16.8±0.9 mg/L (Table 1). The 24-h $IC_{50}$ RDCF value of 14.0±0.9 indicated moderate activity of nitrile (4) against *F. columnare* ALM-00-173 when compared to the drug control florfenicol. Pyranopyran acetate (3) was surprisingly only slightly active against *F. columnare* ALM-00-173 based on a MIC at the highest test concentration of 238 mg/L. Similar results were observed for evaluation of the three test compounds against *E. ictaluri* S02-1039, with nitrile (4) surprisingly also as the most active compound based on a MIC of 0.002±0 mg/L and 24-h $IC_{50}$ of 7.7±1.2 mg/L (Table 2). In comparison to the drug control, pyranopyran nitrile (4) surprisingly had stronger activity than the drug control florfenicol against *E. ictaluri* S02-1039 based on the MIC RDCF value of 0.5±0, but was moderately active based on the 24-h $IC_{50}$ RDCF value of 85.2±3.3. Pyranopyran (2) was moderately toxic against *E. ictaluri* S02-1039 based on a MIC of 19.6±0 mg/L, but it was surprisingly less toxic than the nitrile with a 24-h $IC_{50}$ of 46.1±1.0 mg/L. Because pyranopyran nitrile 4 had strong activity against *E. ictaluri* S02-1039, the minimum bactericidal concentration (MBC) was evaluated and determined to be >177.0 mg/L (the highest test concentration).

The current study is the first to evaluate and report the antibacterial activities of pyranopyran (2), pyranopyran acetate (3), and pyranopyran nitrile (4), against *F. columnare* and *E. ictaluri*, and, more specifically, the surprisingly strong activity of pyranopyran nitrile (4) against *E. ictaluri* S02-1039 based on MIC results.

Pyranopyran (2), pyranopyran acetate (3), and pyranopyran nitrile (4) were also evaluated for phytotoxic activity using the aquatic plant *Lemna paucicostata* (L.) Hegelm. (duckweed). Dose-response curves from the aquatic plant *Lemna paucicostata* (L.) Hegelm. (duckweed) were obtained from experiments conducted. Duckweed was grown and treated as described by Michel et al. (Michel, A., et al., Environ. Toxicol. Chem., 23: 1074-1079 (2004)) with slight modifications. Duckweed stocks were cultivated from single *L. paucicostata* colonies (an aggregate of one mother and two daughter fronds to assure genetic uniformity) in Hoagland's No. 2 basal salt mixture with added iron (1000× Fe-EDTA solution, pH 5.5) in sterile trays. The plants were grown in a growth chamber under the following controlled conditions: continuous light at 26° C. and 120 µmol·s$^{-1}$·m$^{-2}$ photosynthetically active radiation. Hoagland solution was changed every two days. Bioassays were conducted in sterile single small plates (Falcon, Corning Life Science). Each well contained 5 mL with 1% EtOH with or without test compounds. Test compounds were dissolved in EtOH. A graphic template of the six-well plates was used for LemnaTec (LemnaTec, Würselen, Germany) image analysis software. Treatment plates, with two three-frond plants of the approximately same size per well, were incubated during 7 days of treatment. Each treatment was replicated three times. $IC_{50}$ values (concentration of test compound that inhibits growth 50%) were determined with R statistics software. Effects on growth are evaluated by measuring area of the plant fronds with image analysis.

Figure 6:
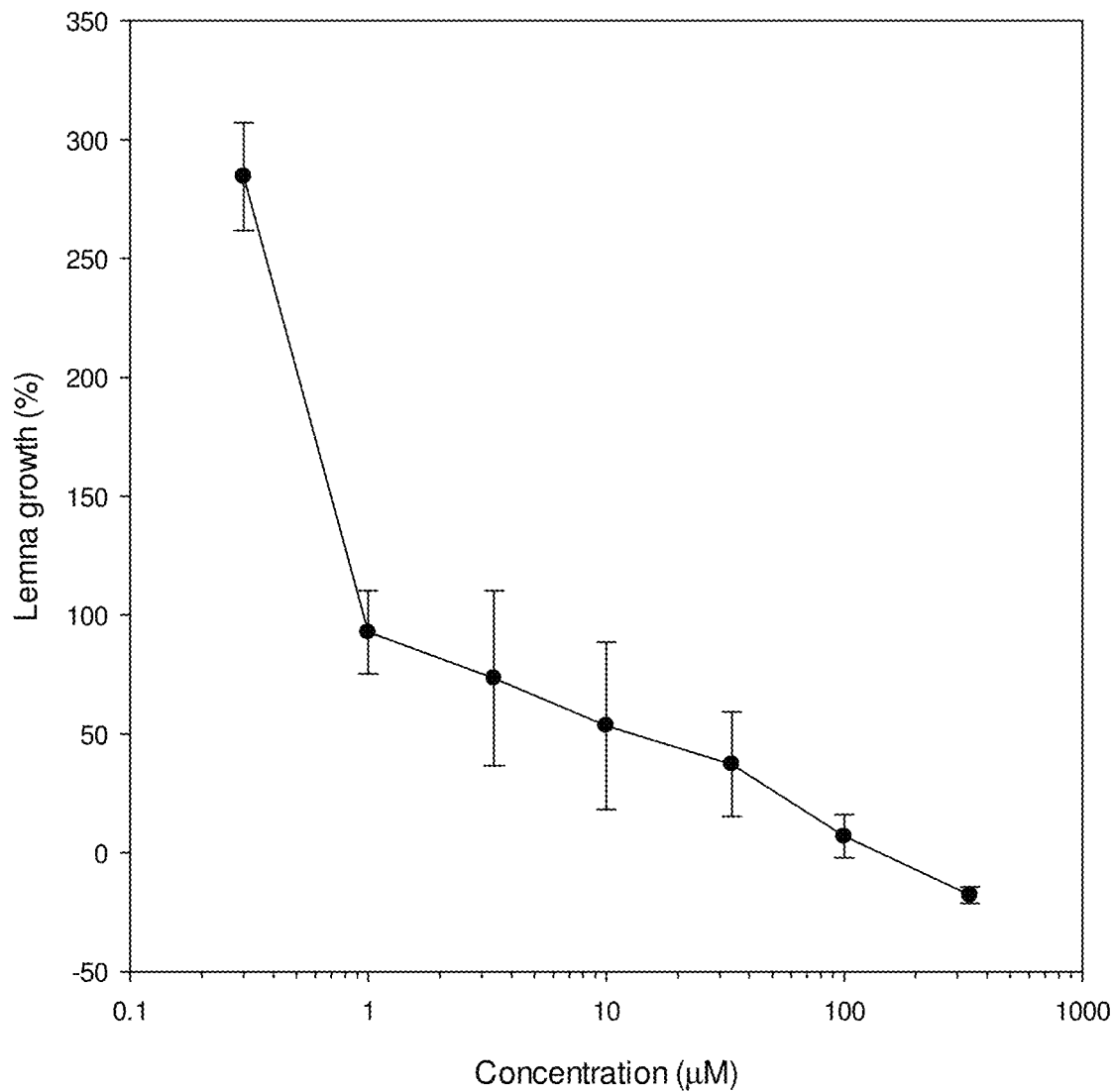
FIG. 6 shows dose/response curves for the nitrile pyranopyran (4) after 6 days of exposure as described below. Error bars are ±1 SE. The control (no test compound)

Surprisingly only pyranopyran nitrile (4) was significantly phytotoxic, with an $IC_{50}$ of less than 1 µM (FIG. 6). At 33 µM and higher some of the plants had no chlorophyll and were necrotic (arrows in FIG. 7). At 100 µM many of the plants were devoid of chlorophyll and necrotic (arrows in FIG. 7). The phytotoxicity of the nitrile pyranopyran (4) in the duckweed bioassay is similar to that of the commercial herbicides isoproturon ($IC_{50}$=0.35 µM), imazethapyr ($IC_{50}$=0.93 µM), and pendimethalin ($IC_{50}$=0.38 µM) in the same bioassay (Michel, A., et al., Environ. Toxicol. Chem., 23: 1074-1079 (2004)). FIG. 7 shows the visual symptoms of the effects of pyranopyran nitrile (4) on the growth of *L. paucicostata*.

All of the references cited herein, including U.S. patents and U.S. patent application Publications, are incorporated by reference in their entirety. Also incorporated by reference in their entirety are the following references: Brunjes, M., et al., Adv. Synth. Catal., 345: 635-642 (2003); Chang, R., et al., Carbohydr. Res., 341: 1998-2004 (2006); Evidente, A., et al., Eur. J. Org. Chem., pages 5564-5570 (2011); Gómez, A., et al., Eur. J. Org. Chem., 7221-7262 (2013); Gong, H., et al., J. Am. Chem. Soc., 129: 1908-1909 (2007)); Györgydeák, Z., and I. F. Pelyvás, Monosaccharide Sugars: Chemical Synthesis by Chain Elongation, Degradation, and Epimerization; Academic Press, San Diego, 1989, pp 100-187); Jarosz, S., Curr. Org. Chem., 12: 985-994 (2008); Levy, D. E., IN The Organic Chemistry of Sugars, D. E. Levy, and P. Fügedi, Eds., Taylor and Francis: Boca Raton, 2006, pp 269-348; Masi, M., et al., J. Agr. Food Chem., 64: 217-225 (2016); Nolen, E. G., et al., J. Carbohyr. Res., 396: 43-47 (2014); Nicolas, L., et al., Angew. Chem. Int. Ed., 51: 11101-11104 (2012); Puckhaber, L. S., et al., J. Agric. Food Chem., 50: 7017-7021 (2002); Romagni, J. G., et al., FEBS Letters, 480: 301-305 (2000); Wang, W., et al., Eur. J. Org. Chem., pages 1053-1059 (2001).

Thus, in view of the above, there is described (in part) the following:

A composition comprising (or consisting essentially of or consisting of) a compound having the following formula:

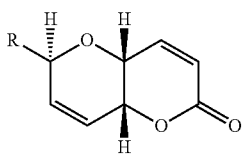

where R is C1-4 alkyl, aryl (e.g., phenyl), —CN, —CH₂OH, —CH(OH)CH₃, —COOH, —CONH₂, —N₃, —NHC(O)R' (e.g., R' is methyl or Ph), —OR' (e.g., R' is methyl, ethyl, cyclohexyl, benzyl, naphthyl, propargyl, or Ph), —CHOC(O)R'CH₃ (e.g., R' is methyl, ethyl, or Ph), —CH₂OC(O)R' (e.g., R' is methyl, ethyl, or Ph), —CH₂C≡CH, —C≡CR" (e.g., R" is methyl, ethyl, hexyl, or PH),

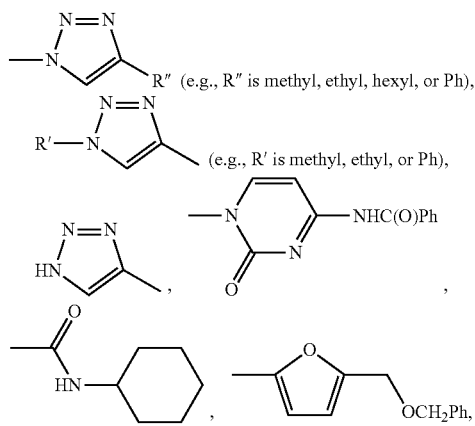

(e.g., R" is methyl, ethyl, or Ph),
where R' is C1-4 alkyl or aryl and R" is H, C1-4 or aryl; and optionally a carrier.

The above composition where the compound is 2,3,4,6-Tetra-O-acetyl-1-deoxy-D-arabino-hex-1-enopyranose (22); where the compound is (2S, 5R, 6R)-5-Hydroxy-6-(trimethylsilyl)ethynyl-5,6-dihydro-2H-pyran-2-yl)methyl acetate (23); where the compound is (2S,5R,6R)-6-Ethynyl-5-hydroxy-5,6-dihydro-2H-pyran-2-yl-methyl acetate (24); where the compound is (2S,5R,6R)-6-Ethenyl-5-hydroxy-5,6-dihydro-2H-pyran-2-yl-methyl acetate (25); where the compound is (2R,3R,6S)-6-(Acetyloxy)methyl]-2-ethenyl-3,6-dihydro-2H-pyran-3-yl prop-2-enoate (26); where the compound is (2S,4aR,8aR)-6-Oxo-2,4a,6,8a-tetrahydropyrano[3,2-b]pyran-2-yl]methyl acetate (27); where the compound is (4aR,6S,8aR)-6-(Hydroxymethyl)-6,8a-dihydropyrano[3,2-b]pyran-2(4aH)-one (28); where the compound is (2S,4aR,8aR)-6-Oxo-2,4a,6,8a-tetrahydropyrano[3,2-b]pyran-2-carboxamide (29); where the compound is ((2R,3R)-3-Acetoxy-6-((trimethylsilyl)ethynyl)-3,6-dihydro-2H-pyran-2-yl)methyl acetate (30); where the compound is (2R,3R)-6-Ethynyl-2-(hydroxymethyl)-3,6-dihydro-2H-pyran-3-ol (31); where the compound is tert-Butyl(((2R,3R)-3-((tert-butyldimethylsilyl)oxy)-6-ethynyl-3,6-dihydro-2H-pyran-2-yl)methoxy)dimethylsilane (32); where the compound is ((2R,3R)-3-((tert-Butyldimethyl silyl)oxy)-6-ethynyl-3,6-dihydro-2H-pyran-2-yl)methanol (33); where the compound is (2S,3R)-3-((tert-Butyldimethylsilyl)oxy)-6-ethynyl-3,6-dihydro-2H-pyran-2-carbaldehyde (34); where the compound is Ethyl (Z)-3-((2R,3R,6S)-3-((tert-butyldimethyl silyl)oxy)-6-ethynyl-3,6-dihydro-2H-pyran-2-yl)acrylate (35); where the compound is (4aR,6S,8aR)-6-Ethynyl-6,8a-dihydropyrano[3,2-b]pyran-2(4aH)-one (36); where the compound is (4aR,6S,8aR)-6-(2H-Tetrazol-5-yl)-6,8a-dihydropyrano[3,2-b]pyran-2(4aH)-one (37); where the compound is not 2,3,4,6-Tetra-O-acetyl-1-deoxy-D-arabino-hex-1-enopyranose (22); where the compound is not (2S, 5R, 6R)-5-Hydroxy-6-(trimethylsilyl)ethynyl-5,6-dihydro-2H-pyran-2-yl)methyl acetate (23); where the compound is not (2S,5R,6R)-6-Ethynyl-5-hydroxy-5,6-dihydro-2H-pyran-2-yl-methyl acetate (24); where the compound is not (2S,5R,6R)-6-Ethenyl-5-hydroxy-5,6-dihydro-2H-pyran-2-yl-methyl acetate (25); where the compound is not (2R,3R,6S)-6-(Acetyloxy)methyl]-2-ethenyl-3,6-dihydro-2H-pyran-3-yl prop-2-enoate (26); where the compound is not (2S,4aR,8aR)-6-Oxo-2,4a,6,8a-tetrahydropyrano[3,2-b]pyran-2-yl]methyl acetate (27); where the compound is not (4aR,6S,8aR)-6-(Hydroxymethyl)-6,8a-dihydropyrano[3,2-b]pyran-2(4aH)-one (28); where the compound is not (2S, 4aR,8aR)-6-Oxo-2,4a,6,8a-tetrahydropyrano[3,2-b]pyran-2-carboxamide (29); where the compound is not ((2R,3R)-3-Acetoxy-6-((trimethylsilyl)ethynyl)-3,6-dihydro-2H-pyran-2-yl)methyl acetate (30); where the compound is not (2R,3R)-6-Ethynyl-2-(hydroxymethyl)-3,6-dihydro-2H-pyran-3-ol (31); where the compound is not tert-Butyl(((2R,3R)-3-((tert-butyldimethylsilyl)oxy)-6-ethynyl-3,6-dihydro-2H-pyran-2-yl)methoxy)dimethylsilane (32); where the compound is not ((2R,3R)-3-((tert-Butyldimethylsilyl)oxy)-6-ethynyl-3,6-dihydro-2H-pyran-2-yl)methanol (33); where the compound is not (2S,3R)-3-((tert-Butyldimethylsilyl)oxy)-6-ethynyl-3,6-dihydro-2H-pyran-2-carbaldehyde (34); where the compound is not Ethyl (Z)-3-((2R,3R,6S)-3-((tert-butyldimethyl silyl)oxy)-6-ethynyl-3,6-dihydro-2H-pyran-2-yl)acrylate (35); where the compound is not (4aR,6S,8aR)-6-Ethynyl-6,8a-dihydropyrano[3,2-b]pyran-2(4aH)-one (36); where the compound is not (4aR,6S,8aR)-6-(2H-Tetrazol-5-yl)-6,8a-dihydropyrano[3,2-b]pyran-2(4aH)-one (37). The above composition, where R is not C1-4 alkyl; where R is not aryl; where R is not —CN; where R is not —CH$_2$OH; where R is not —CH(OH)CH$_3$; where R is not —COOH; where R is not —CONH$_2$; where R is not —N$_3$; where R is not —NHC(O)R'; where R is not —OR', where R is not —CHOC(O)R'CH$_3$; where R is not —CH$_2$OC(O)R'; where R is not —CH$_2$C≡CH; where R is not —C≡CR''; where R is not

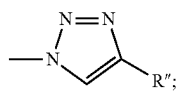

where R is not

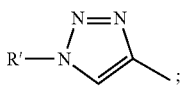

where R is not

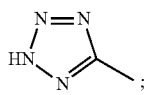

where R is not

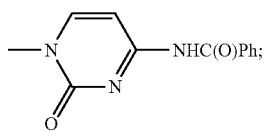

where R is not

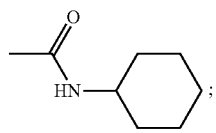

where R is not

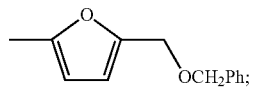

where R is not

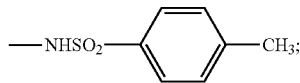

where R is not

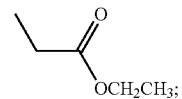

where R is not

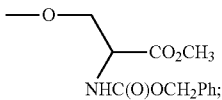

or where R is not —SR''. The above composition, wherein said compound has the following formula:

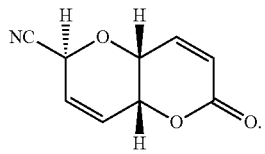

4 (-)-Diplopyrone Nitrile

A method for killing microorganisms or weeds on or in an object or area, said method comprising contacting said object or area with an effective microorganisms or weeds killing amount of the above composition and optionally a carrier.

A method of making (4aR,6S,8aR)-6-((R)-1-hydroxyethyl)-6,8a-dihydropyrano[3,2-b]pyran-2-(4aH)-one (2), said method comprising (or consisting essentially of or consisting of)

(a) reacting 1,2:3,4-diisopropylidene-α-D-galactopyranose (12) in a halocarbon solvent (e.g., dichloromethane) with 2,2,6,6-tetramethyl-1-piperidinyloxy in the presence of bis(acetoxy)iodo-benzene to produce 1,2;3,4-di-O-isopropylidene-α-D-galacto-1,6-dialdo-hexopyranose (13), (b) reacting 1,2;3,4-di-O-isopropylidene-α-D-galacto-1,6-dialdo-hexopyranose (13) with methyl(triisopropoxy)titanium in a halocarbon solvent (e.g., dichloromethane) to produce 7-deoxy-1,2;3,4-di-O-isopropylidene-D-glycero-α-D-galacto-heptopyranose (14), (c) reacting 7-deoxy-1,2;3,4-di-O-isopropylidene-D-glycero-α-D-galacto-heptopyranose (14) with acetic acid/water and then acetic anhydride to produce 1,2,3,4,6-penta-O-acetyl-7-deoxy-D-glycero-D-galacto-heptopyranoside (15), (d) reacting 1,2,3,4,6-penta-O-acetyl-7-deoxy-D-glycero-D-galacto-heptopyranoside (15) with HBr solution (e.g., in glacial acetic acid) to produce 2,3,4,6-tetra-O-acetyl-7-deoxy-D-glycero-α-D-galacto-heptopyranoside bromide (16), (e) reacting 2,3,4,6-tetra-O-acetyl-7-deoxy-D-glycero-α-D-galacto-heptopyranoside bromide (16) with tetra-n-butylammonium bromide, an amine base (e.g., 1,8-diazabicyclo[5.4.0]undec-7-ene), and a polar aprotic solvent (e.g., acetonitrile) to produce 2,3,4,6-tetra-O-acetyl-7-deoxy-1,5-anhydro-D-gluco-hept-1-enitol (17), (f) reacting 2,3,4,6-tetra-O-acetyl-7-deoxy-1,5-anhydro-D-gluco-hept-1-enitol (17) in a halocarbon solvent (e.g., dichloromethane) with bis(trimethylsilyl)acetylene and a Lewis acid catalyst (e.g., tin tetrachoride (SnCl4)) to produce (R)-1-((2S,5R,6R)-5-hydroxy-6-((trimethylsilyl)ethynyl)-5,6-dihydro-2H-pyran-2-yl)ethyl acetate (18), (g) reacting (R)-1-((2S,5R,6R)-5-hydroxy-6-((trimethylsilyl)ethynyl)-5,6-dihydro-2H-pyran-2-yl)ethyl acetate (18) in an ether solvent (e.g., THF; tetrahydrofuran) with tetrabutylammonium fluoride to produce (R)-1-((2S,5R,6R)-5-hydroxy-6-ethynyl)-5,6-dihydro-2H-pyran-2-yl)ethyl acetate (19), (h) reacting (R)-1-((2S,5R,6R)-5-hydroxy-6-ethynyl)-5,6-dihydro-2H-pyran-2-yl)ethyl acetate (19) in a solvent (ethyl acetate; what generic type of solvent?) with a catalyst (e.g., hydrogenation catalyst like 5% Pd/CaCO3), hydrogen, and quinoline to produce (R)-1-((2S,5R,6R)-5-hydroxy-6-vinyl-5,6-dihydro-2H-pyran-2-yl)ethyl acetate (20), (i) reacting (R)-1-((2S,5R,6R)-5-hydroxy-6-vinyl-5,6-dihydro-2H-pyran-2-yl)ethyl acetate (20) in a halocarbon solvent (e.g., dichloromethane) with acryloyl chloride and triethylamine to produce (2S,3R,6S)-6-((R)-1-acetoxyethyl)2-vinyl-3,6-dihydro-2H-pyran-2-yl)ethyl acrylate (21), (j) reacting (2S,3R,6S)-6-((R)-1-acetoxyethyl)2-vinyl-3,6-dihydro-2H-pyran-2-yl)ethyl acrylate (21) in a hydrocarbon solvent (e.g., anhydrous toluene) with an alkene metathesis catalyst (e.g., Grubbs II or variant) and anhydrous toluene to produce (4aR,6S,8aR)-6-((R)-1-acetoxyethyl)-6,8a-dihydropyrano[3,2-b]pyran-2-(4aH)-one (3), and (k) reacting (4aR,6S,8aR)-6-((R)-1-acetoxyethyl)-6,8a-dihydropyrano[3,2-b]pyran-2-(4aH)-one (3) in an ether solvent (e.g., tetrahydrofuran, THF) with water and lipase (e.g., Lipase PS) to produce (4aR,6S,8aR)-6-((R)-1-hydroxyethyl)-6,8a-dihydropyrano[3,2-b]pyran-2-(4aH)-one (2).

A method of making (4aR,6S,8aR)-6-cyano-6,8a-dihydropyrano-[3,2-b]pyran-2(4aH)-one (4), said method comprising (or consisting essentially of or consisting of)

(a) reacting 3,4,6-tri-O-acetyl-D-galactal (5) with trimethylsilyl cyanide, Lewis acid (e.g., boron trifluoride etherate), and trimethylsilyl cyanide, to produce 4,6-di-O-acetyl-2,3-dideoxy-α-D-threo-hexopyranosyl cyanide (6), (b) reacting 4,6-di-O-acetyl-2,3-dideoxy-α-D-threo-hexopyranosyl cyanide (6) in an alcohol solvent (e.g., methanol) with p-toluenesulfonic acid monohydrate to produce 2,3-dideoxy-α-D-threo-hex-2-enopyranosyl cyanide (7), (c) reacting 2,3-dideoxy-α-D-threo-hex-2-enopyranosyl cyanide (7) in a solvent (e.g., anhydrous dichloromethane like DMF; ether solvent like THF; dimethylformamide; aromatic amine base like 2,6-lutidine; polar aprotic solvent like acetonitrile) with imidazole and tert-butyldimethylsilyl chloride to produce 4,6-di-O-tert-butyldimethylsilyl-2,3-dideoxy-α-D-threo-hex-2-enopyranosyl cyanide (8), (d) reacting 4,6-di-O-tert-butyldimethylsilyl-2,3-dideoxy-α-D-threo-hex-2-enopyranosyl cyanide (8) with pyridinium p-toluenesulfonate in an anhydrous alcohol solvent (e.g., anhydrous methanol) to produce 4-O-tert-butyldimethylsilyl-2,3-dideoxy-α-D-threo-hex-2-enopyranosyl cyanide (9), (e) reacting 4-O-tert-butyldimethylsilyl-2,3-dideoxy-α-D-threo-hex-2-enopyranosyl cyanide (9) with halocarbon solvent (e.g., anhydrous dichloromethane), anhydrous dimethyl sulfoxide, an oxidant (e.g., sulfur trioxide-pyridine complex), and diisopropylethylamine to produce (2S,5R,6S)-5-(tert-butyldimethylsilyl)oxy)-6-formyl-5,6-dihydro-2H-pyran-2-carbonitrile (10), (f) reacting (2S,5R,6S)-5-(tert-butyldimethylsilyl)oxy)-6-formyl-5,6-dihydro-2H-pyran-2-carbonitrile (10) in an alcohol solvent (e.g., methanol) with (carbethoxymethylene)-triphenylphosphorane to produce ethyl (Z)-3-((2R,3R,6S)-3-((tert-butyldimethylsilyl)oxy)-6-cyano-3,6-dihydro-2H-pyran-2-yl)acrylate (11), and (g) reacting ethyl (Z)-3-((2R,3R,6S)-3-((tert-butyldimethylsilyl)oxy)-6-cyano-3,6-dihydro-2H-pyran-2-yl)acrylate (11) in an alcohol solvent (e.g., methanol) with p-toluenesulfonate to produce (4aR,6S,8aR)-6-cyano-6,8a-dihydropyrano-[3,2-b]pyran-2(4aH)-one (4).

A composition comprising (or consisting essentially of or consisting of) at least one compound having the following formula selected from the group consisting of (4aR,6S,8aR)-6-cyano-6,8a-dihydropyrano-[3,2-b]pyran-2(4aH)-one (4); 4,6-di-O-tert-butyldimethylsilyl-2,3-dideoxy-α-D-threo-hex-2-enopyranosyl cyanide (8); (9); (2S,5R,6S)-5-(tert-butyldimethylsilyl)oxy)-6-formyl-5,6-dihydro-2H-pyran-2-carbonitrile (10); ethyl (Z)-3-((2R,3R,6S)-3-((tert-butyldimethylsilyl)oxy)-6-cyano-3,6-dihydro-2H-pyran-2-yl)acrylate (11); (4aR,6S,8aR)-6-((R)-1-hydroxyethyl)-6,8a-dihydropyrano[3,2-b]pyran-2-(4aH)-one (2); (4aR,6S,8aR)-6-((R)-1-acetoxyethyl)-6,8a-dihydropyrano[3,2-b]pyran-2-(4aH)-one (3); 2,3,4,6-tetra-O-acetyl-7-deoxy-1,5-anhydro-D-gluco-hept-1-enitol (17); (R)-1-((2S,5R,6R)-5-hydroxy-6-((trimethylsilyl)ethynyl)-5,6-dihydro-2H-pyran-2-yl)ethyl acetate (18); (R)-1-((2S,5R,6R)-5-hydroxy-6-ethynyl)-5,6-dihydro-2H-pyran-2-yl)ethyl acetate (19); (R)-1-((2S,5R,6R)-5-hydroxy-6-vinyl-5,6-dihydro-2H-pyran-2-yl)ethyl acetate (20); (2S,3R,6S)-6-((R)-1-acetoxyethyl)2-vinyl-3,6-dihydro-2H-pyran-2-yl)ethyl acrylate (21); and mixtures thereof, and optionally a carrier.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . . Silence in the specification may be used to establish written description support for a negative limitation. As an example, in Exparte Lin (No. 2009-0486, at 2, 6 (B.P.A.I. May 7, 2009)) the negative limitation was added by amendment . . . . In other words, the inventor argued an example that passively complied with the requirements of the negative limitation . . . was sufficient to provide support . . . . This case shows that written description support for a negative limitation can be found by one or more disclosures of an embodiment that obeys what is required by the negative limitation . . . ."

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Results of bioassay evaluations of diplopyrone derivatives for antibacterial activity against *Flavobacterium columnare* ALM-00-173. Numbers in parentheses are the standard error of the means.

| Test material | MIC[a] | 24-h IC$_{50}$[b] | MTT 24-h IC$_{50}$[c] | $\dfrac{MIC^{a}}{RDCF^{d}}$ | $\dfrac{\text{24-h } IC_{50}^{b}}{RDCF^{d}}$ |
|---|---|---|---|---|---|
| Florfenicol | 0.36 | 0.54 | | | |
| Pyranopyran (2) | 196.0 (0) | 76.4 (2.0) | 78.4 (0) | 544.4 (0) | 141.6 (3.6) |
| Pyranopyran acetate (3) | 238.0 (0) | >238.0 | >238.0 | 661.1 (0) | >440.7 |
| Pyranopyran nitrile (4) | 17.7 (0) | 7.5 (0.5) | 16.8 (0.9) | 49.2 (0) | 14.0 (0.9) |
| Florfenicol | 0.36 | 0.69 | | | |
| Desmethylpyranopyran | 182.0 (0) | 76.4 (3.6) | 79.2 (2.7) | 505.6 (0) | 109.1 (2.1) |
| Desmethylpyranopyran acetate | 224.0 (0) | >224.0 | >224.0 | 622.2 (0) | >329.4 |
| Pyranopyran amide | 107.3 (87.8) | 54.6 (2.0) | 75.1 (1.0) | 297.9 (243.8) | 38.5 (31.7) |

[a]MIC = Minimum inhibitory concentration in mg/L.

[b]24-h IC$_{50}$ = 50% inhibition concentration in mg/L.

[c]24-h IC$_{50}$ (mg/L) as measurement of cell viability using the tetrazolium bromide dye MTT.

[d]RDCF = Relative-to-drug-control florfenicol; values closer to 1.0 indicate higher antibacterial activity compared to florfenicol.

TABLE 2

Results of bioassay evaluations of diplopyrone derivatives for antibacterial activity against *Edwardsiella ictaluri* S02-1039. Numbers in parentheses are the standard error of the means.

| Test material | MIC[a] | 24-h IC$_{50}$[b] | MTT 24-h IC$_{50}$[c] | $\dfrac{MIC^{a}}{RDCF^{d}}$ | $\dfrac{\text{24-h } IC_{50}^{b}}{RDCF^{d}}$ |
|---|---|---|---|---|---|
| Florfenicol | 0.36 | 0.14 | | | |
| Pyranopyran (2) | 19.6 (0) | 46.1 (1.0) | 22.1 (9.3) | 54.4 (0) | 329.0 (7.0) |
| Pyranopyran acetate (3) | 238.0 (0) | 165.4 (1.2) | 90.4 (4.8) | 661.1 (0) | 1,181.5 (8.5) |
| Pyranopyran nitrile (4) | 0.002 (0) | 7.7 (1.2) | 64.6 (4.4) | 0.5 (0) | 85.2 (3.3) |
| Florfenicol | 0.36 | 0.18 | | | |
| Desmethyl-pyranopyran (28) | 18.2 (0) | 48.2 (2.7) | 14.7 (9.0) | 50.6 (0) | 358.5 (33.5) |
| Desmethylpyranopyra acetate (27) | 22.4 (0) | 39.2 (1.1) | 35.8 (4.5) | 62.2 (0) | 290.5 (2.5) |
| Pyranopyran amide (29) | 19.5 (0) | 20.5 (2.9) | 16.6 (8.8) | 54.2 (0) | 135.8 (10.5) |

[a]MIC = Minimum inhibitory concentration in mg/L.

[b]24-h IC$_{50}$ = 50% inhibition concentration in mg/L.

[c]24-h IC$_{50}$ (mg/L) as measurement of cell viability using the tetrazolium bromide dye MTT.

[d]RDCF = Relative-to-drug-control florfenicol; values closer to 1.0 indicate higher antibacterial activity compared to florfenicol.

TABLE 3

Crystal data and structure refinement for (4).

| | |
|---|---|
| Identification code | compound (4) |
| Empirical formula | $C_9H_7NO_3$ |
| Formula weight | 177.16 |
| Temperature | 100.0 K |
| Wavelength | 0.71073 Å |
| Crystal system | Orthorhombic |
| Space group | $P2_12_12_1$ |
| Unit cell dimensions | a = 6.9595(6) Å    a = 90°. |
| | b = 10.7062(9) Å   b = 90°. |
| | c = 11.3837(10) Å  g = 90°. |
| Volume | 848.20(13) Å$^3$ |
| Z | 4 |
| Density (calculated) | 1.387 Mg/m$^3$ |
| Absorption coefficient | 0.106 mm$^{-1}$ |
| F(000) | 368 |
| Crystal size | 0.4 × 0.3 × 0.2 mm$^3$ |
| Theta range for data collection | 2.612 to 36.270°. |
| Index ranges | −11 <= h <= 11, −17 <= k <= 17, |
| | −18 <= l <= 17 |
| Reflections collected | 33419 |
| Independent reflections | 4104 [R(int) = 0.0205] |
| Completeness to theta = 26.000° | 100.0% |
| Absorption correction | Semi-empirical from equivalents |
| Max. and min. transmission | 0.7471 and 0.7158 |
| Refinement method | Full-matrix least-squares on F$^2$ |
| Data/restraints/parameters | 4104/0/118 |
| Goodness-of-fit on F$^2$ | 1.108 |
| Final R indices [I > 2sigma(I)] | R1 = 0.0289, wR2 = 0.0795 |
| R indices (all data) | R1 = 0.0301, wR2 = 0.0805 |
| Absolute structure parameter | −0.07(10) |
| Extinction coefficient | n/a |
| Largest diff. peak and hole | 0.436 and −0.167 e · Å$^{-3}$ |

We claim:

1. A composition comprising a compound having the following formula:

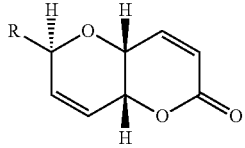

where R is C1-4 alkyl, aryl, —CN, —CH$_2$OH, —COOH, —CONH$_2$, —N$_3$, —NHC(O)R', —CHOC(O)R'CH$_3$, —CH$_2$OC(O)R',

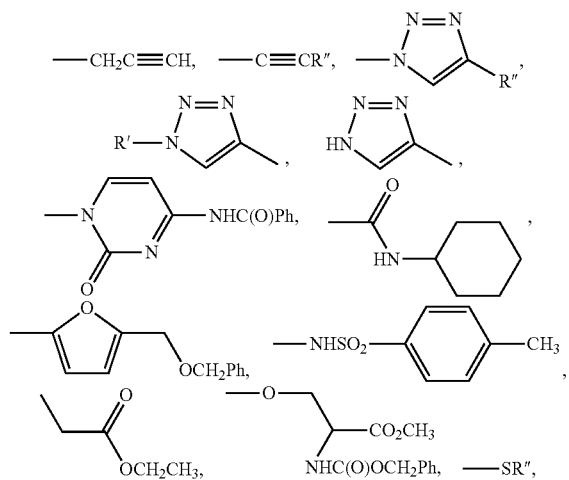

where R' is C1-4 alkyl or aryl and R" is H, C1-4 or aryl; and optionally a carrier.

2. The composition according to claim 1, wherein said compound has the following formula:

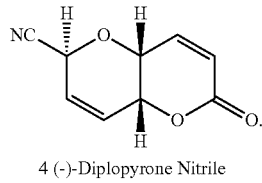 [SMILES: N#C[C@@H]1C=C[C@H]2OC(=O)C=C[C@H]2O1]

4 (-)-Diplopyrone Nitrile

3. A method for killing microorganisms or weeds on or in an object or area, said method comprising contacting said object or area with an effective microorganisms or weeds killing amount of the composition according to claim 1 and optionally a carrier.

4. A method of making (4aR,6S,8aR)-6-(R)-1-hydroxyethyl)-6,8a-dihydropyrano[3,2-b]pyran-2-(4aH)-one (2), said method comprising
    (a) reacting 1,2:3,4-diisopropylidene-α-D-galactopyranose (12) in a halocarbon solvent with 2,2,6,6-tetramethyl-1-piperidinyloxy in the presence of bis(acetoxy) iodo-benzene to produce 1,2;3,4-di-O-isopropylidene-α-D-galacto-1,6-dialdo-hexopyranose (13),
    (b) reacting 1,2;3,4-di-O-isopropylidene-α-D-galacto-1,6-dialdo-hexopyranose (13) with methyl(triisopropoxy)titanium in a halocarbon solvent to produce 7-deoxy-1,2;3,4-di-O-isopropylidene-D-glycero-α-D-galacto-heptopyranose (14),
    (c) reacting 7-deoxy-1,2;3,4-di-O-isopropylidene-D-glycero-α-D-galacto-heptopyranose (14) with acetic acid/water and then acetic anhydride to produce 1,2,3,4,6-penta-O-acetyl-7-deoxy-D-glycero-D-galacto-heptopyranoside (15),
    (d) reacting 1,2,3,4,6-penta-O-acetyl-7-deoxy-D-glycero-D-galacto-heptopyranoside (15) with HBr solution to produce 2,3,4,6-tetra-O-acetyl-7-deoxy-D-glycero-α-D-galacto-heptopyranoside bromide (16),
    (e) reacting 2,3,4,6-tetra-O-acetyl-7-deoxy-D-glycero-α-D-galacto-heptopyranoside bromide (16) with tetra-n-butylammonium bromide, [1,8-diazabicyclo[5.4.0]undec-7-ene], and a polar aprotic solvent to produce 2,3,4,6-tetra-O-acetyl-7-deoxy-1,5-anhydro-D-glucohept-1-enitol (17),
    (f) reacting 2,3,4,6-tetra-O-acetyl-7-deoxy-1,5-anhydro-D-gluco-hept-1-enitol (17) in a halocarbon solvent with bis(trimethylsilyl)acetylene and a Lewis acid catalyst to produce (R)-1-((2S,5R,6R)-5-hydroxy-6-((trimethylsilyl)ethynyl)-5,6-dihydro-2H-pyran-2-yl)ethyl acetate (18),
    (g) reacting (R)-1-((2S,5R,6R)-5-hydroxy-6-((trimethylsilyl)ethynyl)-5,6-dihydro-2H-pyran-2-yl)ethyl acetate (18) in an ether solvent with tetrabutylammonium fluoride to produce (R)-1-((2S,5R,6R)-5-hydroxy-6-ethynyl)-5,6-dihydro-2H-pyran-2-yl)ethyl acetate (19),
    (h) reacting (R)-1-((2S,5R,6R)-5-hydroxy-6-ethynyl)-5,6-dihydro-2H-pyran-2-yl)ethyl acetate (19) in a solvent with a hydrogenation catalyst, hydrogen, and quinoline to produce (R)-1-((2S,5R,6R)-5-hydroxy-6-vinyl-5,6-dihydro-2H-pyran-2-yl)ethyl acetate (20),
    (i) reacting (R)-1-((2S,5R,6R)-5-hydroxy-6-vinyl-5,6-dihydro-2H-pyran-2-yl)ethyl acetate (20) in a halocarbon solvent with acryloyl chloride and triethylamine to produce (2S,3R,6S)-6-((R)-1-acetoxyethyl)2-vinyl-3,6-dihydro-2H-pyran-2-yl)ethyl acrylate (21), (j) reacting (2S,3R,6S)-6-((R)-1-acetoxyethyl)2-vinyl-3,6-dihydro-2H-pyran-2-yl)ethyl acrylate (21) in a hydrocarbon solvent with an alkene metathesis catalyst and anhydrous toluene to produce (4aR,6S,8aR)-6-(R)-1-acetoxyethyl)-6,8a-dihydropyrano[3,2-b]pyran-2-(4aH)-one (3), and (k) reacting (4aR,6S,8aR)-6-((R)-1-acetoxyethyl)-6,8a-dihydropyrano[3,2-b]pyran-2-(4aH)-one (3) in an ether solvent with water and lipase to produce (4aR,6S,8aR)-6-((R)-1-hydroxyethyl)-6,8a-dihydropyrano[3,2-b]pyran-2-(4aH)-one (2).

5. A method of making (4aR,6S,8aR)-6-cyano-6,8a-dihydropyrano-[3,2-b]pyran-2(4aH)-one (4), said method comprising (a) reacting 3,4,6-tri-O-acetyl-D-galactal (5) with trimethylsilyl cyanide, Lewis acid, and trimethylsilyl cyanide to produce 4,6-di-O-acetyl-2,3-dideoxy-α-D-threo-hexopyranosyl cyanide (6), (b) reacting 4,6-di-O-acetyl-2,3-dideoxy-α-D-threo-hexopyranosyl cyanide (6) in an alcohol solvent with p-toluenesulfonic acid monohydrate to produce 2,3-dideoxy-α-D-threo-hex-2-enopyranosyl cyanide (7), (c) reacting 2,3-dideoxy-α-D-threo-hex-2-enopyranosyl cyanide (7) in a solvent with imidazole and tert-butyldimethylsilyl chloride to produce 4,6-di-O-tert-butyldimethylsilyl-2,3-dideoxy-α-D-threo-hex-2-enopyranosyl cyanide (8), (d) reacting 4,6-di-O-tert-butyldimethylsilyl-2,3-dideoxy-α-D-threo-hex-2-enopyranosyl cyanide (8) with pyridinium p-toluenesulfonate in an anhydrous alcohol solvent to produce 4-O-tert-butyldimethylsilyl-2,3-dideoxy-α-D-threo-hex-2-enopyranosyl cyanide (9), (e) reacting 4-O-tert-butyldimethylsilyl-2,3-dideoxy-α-D-threo-hex-2-enopyranosyl cyanide (9) with halocarbon solvent, anhydrous dimethyl sulfoxide, and diisopropylethylamine to produce (2S,5R,6S)-5-(tert-butyldimethylsilyl)oxy)-6-formyl-5,6-dihydro-2H-pyran-2-carbonitrile (10), (f) reacting (2S,5R,6S)-5-(tert-butyldimethylsilyl)oxy)-6-formyl-5,6-dihydro-2H-pyran-2-carbonitrile (10) in an alcohol solvent with (carbethoxymethylene)-triphenylphosphorane to produce ethyl (Z)-3-((2R,3R,6S)-3-((tert-butyldimethylsilyl)oxy)-6-cyano-3,6-dihydro-2H-pyran-2-yl)acrylate (11), and (g) reacting ethyl (Z)-3-((2R,3R,6S)-3-((tert-butyldimethylsilyl)oxy)-6-cyano-3,6-dihydro-2H-pyran-2-yl)acrylate (11) in an alcohol solvent with p-toluenesulfonate to produce (4aR,6S,8aR)-6-cyano-6,8a-dihydropyrano-[3,2-b]pyran-2(4aH)-one (4).

6. A composition comprising at least one compound selected from the group consisting of (4aR,6S,8aR)-6-cyano-6,8a-dihydropyrano-[3,2-b]pyran-2(4aH)-one (4); 4,6-di-O-tert-butyldimethylsilyl-2,3-dideoxy-α-D-threo-hex-2-enopyranosyl cyanide (8); (9); (2S,5R,6S)-5-(tert-butyldimethylsilyl)oxy)-6-formyl-5,6-dihydro-2H-pyran-2-carbonitrile (10); ethyl (Z)-3-((2R,3R,6S)-3-((tert-butyldimethylsilyl)oxy)-6-cyano-3,6-dihydro-2H-pyran-2-yl)acrylate (11); (4aR,6S,8aR)-6-((R)-1-acetoxyethyl)-6,8a-dihydropyrano [3,2-b]pyran-2-(4aH)-one (3); 2,3,4,6-tetra-0-acetyl-7-deoxy-1,5-anhydro-D-gluco-hept-1-enitol (17); (R)-1-((2S,5R,6R)-5-hydroxy-6-((trimethylsilyl)ethynyl)-5,6-dihydro-2H-pyran-2-yl)ethyl acetate (18); (R)-1-((2S,5R,6R)-5-hydroxy-6-ethynyl)-5,6-dihydro-2H-pyran-2-yl)ethyl acetate (19); (R)-1-((2S,5R,6R)-5-hydroxy-6-vinyl-5,6-dihydro-2H-pyran-2-yl)ethyl acetate (20); (2S,3R,6S)-6-((R)-1-acetoxyethyl)2-vinyl-3,6-dihydro-2H-pyran-2-yl)ethyl acrylate (21); and mixtures thereof; and optionally a carrier.

* * * * *